US012618818B2

(12) United States Patent
Sajja et al.

(10) Patent No.: US 12,618,818 B2
(45) Date of Patent: May 5, 2026

(54) ARRAYS OF GAS SENSOR DEVICE PACKAGES, AND RELATED METHODS

(71) Applicant: Nevada Nanotech Systems Inc., Sparks, NV (US)

(72) Inventors: Vijay Mohan Sajja, Fremont, CA (US); Steven W. Malekos, Sparks, NV (US); Dean A. Hopkins, Reno, NV (US); Ronald J. Mack, Reno, NV (US)

(73) Assignee: Nevada Nanotech Systems Inc., Sparks, NV (US)

( * ) Notice: Subject to any disclaimer, the term of this patent is extended or adjusted under 35 U.S.C. 154(b) by 490 days.

(21) Appl. No.: 18/043,500

(22) PCT Filed: Aug. 25, 2021

(86) PCT No.: PCT/US2021/071279
§ 371 (c)(1),
(2) Date: Feb. 28, 2023

(87) PCT Pub. No.: WO2022/051743
PCT Pub. Date: Mar. 10, 2022

(65) Prior Publication Data
US 2024/0044856 A1 Feb. 8, 2024

Related U.S. Application Data

(60) Provisional application No. 62/706,670, filed on Sep. 2, 2020.

(51) Int. Cl.
*G01N 33/00* (2006.01)
(52) U.S. Cl.
CPC ..... *G01N 33/0031* (2013.01); *G01N 33/0063* (2013.01)

(58) Field of Classification Search
CPC ...................... G01N 33/0031; G01N 33/0033
USPC ......................................................... 73/23.2
See application file for complete search history.

(56) References Cited

U.S. PATENT DOCUMENTS

| | | | |
|---|---|---|---|
| 5,948,988 A | 9/1999 | Bodin | |
| 6,351,982 B1 | 3/2002 | Tindall et al. | |
| 6,907,789 B2 | 6/2005 | Bodin | |
| 7,002,241 B1 | 2/2006 | Mostafazadeh et al. | |
| 7,723,141 B2 | 5/2010 | Robert | |
| 8,049,287 B2 | 11/2011 | Combi et al. | |

(Continued)

FOREIGN PATENT DOCUMENTS

WO 2007042336 A2 4/2007

OTHER PUBLICATIONS

Baltes et al., "CMOS-Based Microsensors and Packaging", Sensors and Actuators, A 92, (2001), 9 pages.

(Continued)

*Primary Examiner* — Nathaniel T Woodward
(74) *Attorney, Agent, or Firm* — RAY QUINNEY & NEBEKER; Daniel J. Bezdjian

(57) ABSTRACT

An array of gas sensor device packages comprises a plurality of gas sensor device packages, each gas sensor device package comprising a lead frame including bond pads and at least one gas sensor die in electrical communication with the bond pads. The array further comprises a protective covering over the plurality of gas sensor device packages. Related gas sensor device packages and arrays and methods of forming the arrays are also disclosed.

29 Claims, 19 Drawing Sheets

(56) References Cited

U.S. PATENT DOCUMENTS

| | | | |
|---|---|---|---|
| 8,318,525 B2 | 11/2012 | Davies et al. | |
| 8,884,382 B2 | 11/2014 | Stetter et al. | |
| 9,482,592 B2 | 11/2016 | Huseynov et al. | |
| 9,618,490 B2 | 4/2017 | Paik et al. | |
| 9,754,848 B2 | 9/2017 | Jun et al. | |
| 2001/0011762 A1 | 8/2001 | Corisis et al. | |
| 2006/0032745 A1* | 2/2006 | Davies .................. | G01N 27/16 |
| | | | 204/431 |
| 2007/0102639 A1 | 5/2007 | Cutler et al. | |
| 2007/0218585 A1 | 9/2007 | Robert | |
| 2011/0241197 A1 | 10/2011 | Theuss | |
| 2014/0346623 A1* | 11/2014 | Elian .................... | G01L 19/147 |
| | | | 438/51 |
| 2015/0177171 A1 | 6/2015 | Kim et al. | |
| 2015/0362451 A1 | 12/2015 | Hunziker et al. | |

OTHER PUBLICATIONS

International Search Report from International Application No. PCT/US2021/071279, mailed Feb. 14, 2022, 4 pages.
International Written Opinion from International Application No. PCT/US2021/071279, mailed Feb. 14, 2022, 11 pages.
Invitation to Pay Additional Fees from International Application No. PCT/US2021/071279, mailed Dec. 2, 2021, 2 pages.

* cited by examiner

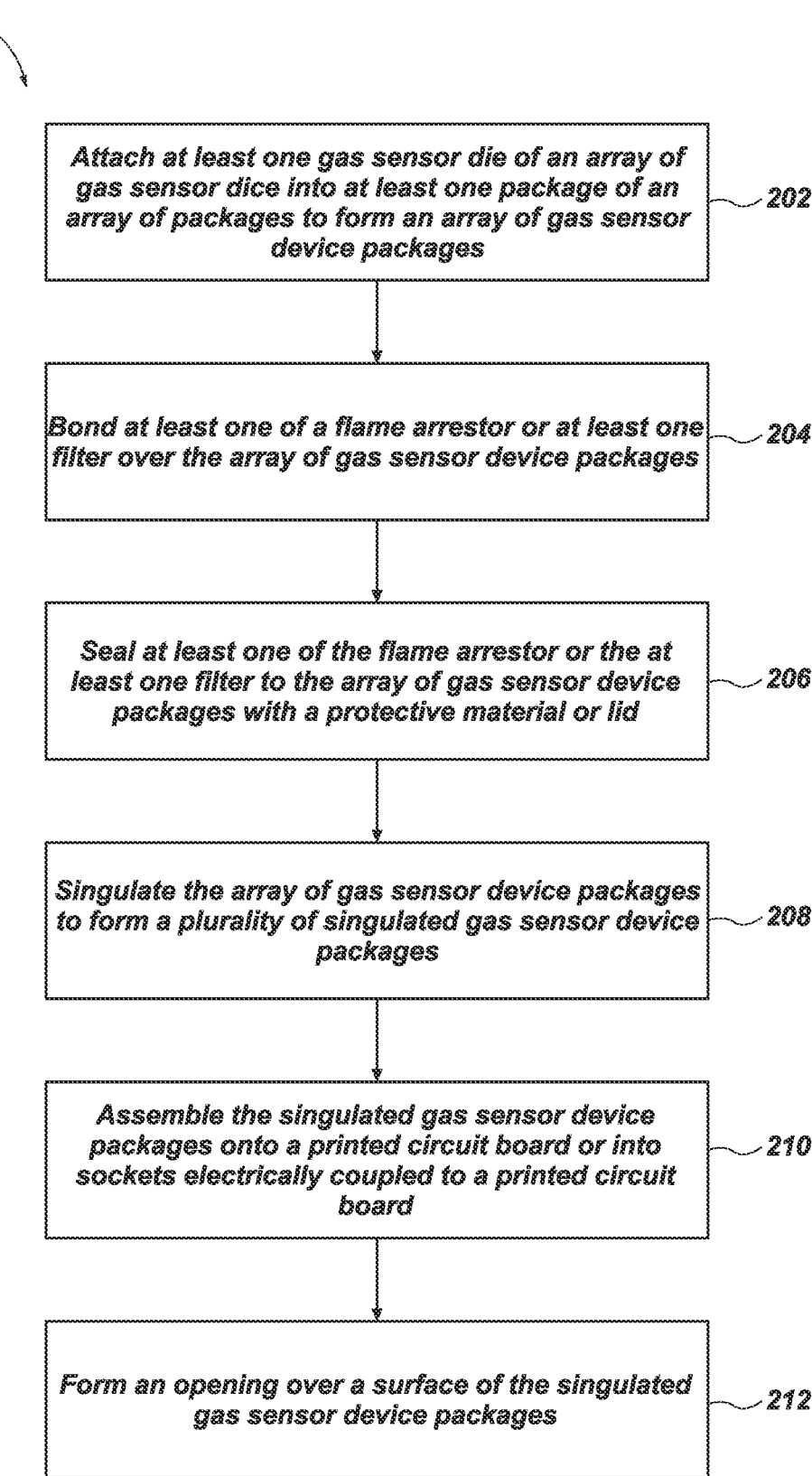

*200*

Attach at least one gas sensor die of an array of gas sensor dice into at least one package of an array of packages to form an array of gas sensor device packages — *202*

Bond at least one of a flame arrestor or at least one filter over the array of gas sensor device packages — *204*

Seal at least one of the flame arrestor or the at least one filter to the array of gas sensor device packages with a protective material or lid — *206*

Singulate the array of gas sensor device packages to form a plurality of singulated gas sensor device packages — *208*

Assemble the singulated gas sensor device packages onto a printed circuit board or into sockets electrically coupled to a printed circuit board — *210*

Form an opening over a surface of the singulated gas sensor device packages — *212*

*FIG. 2A*

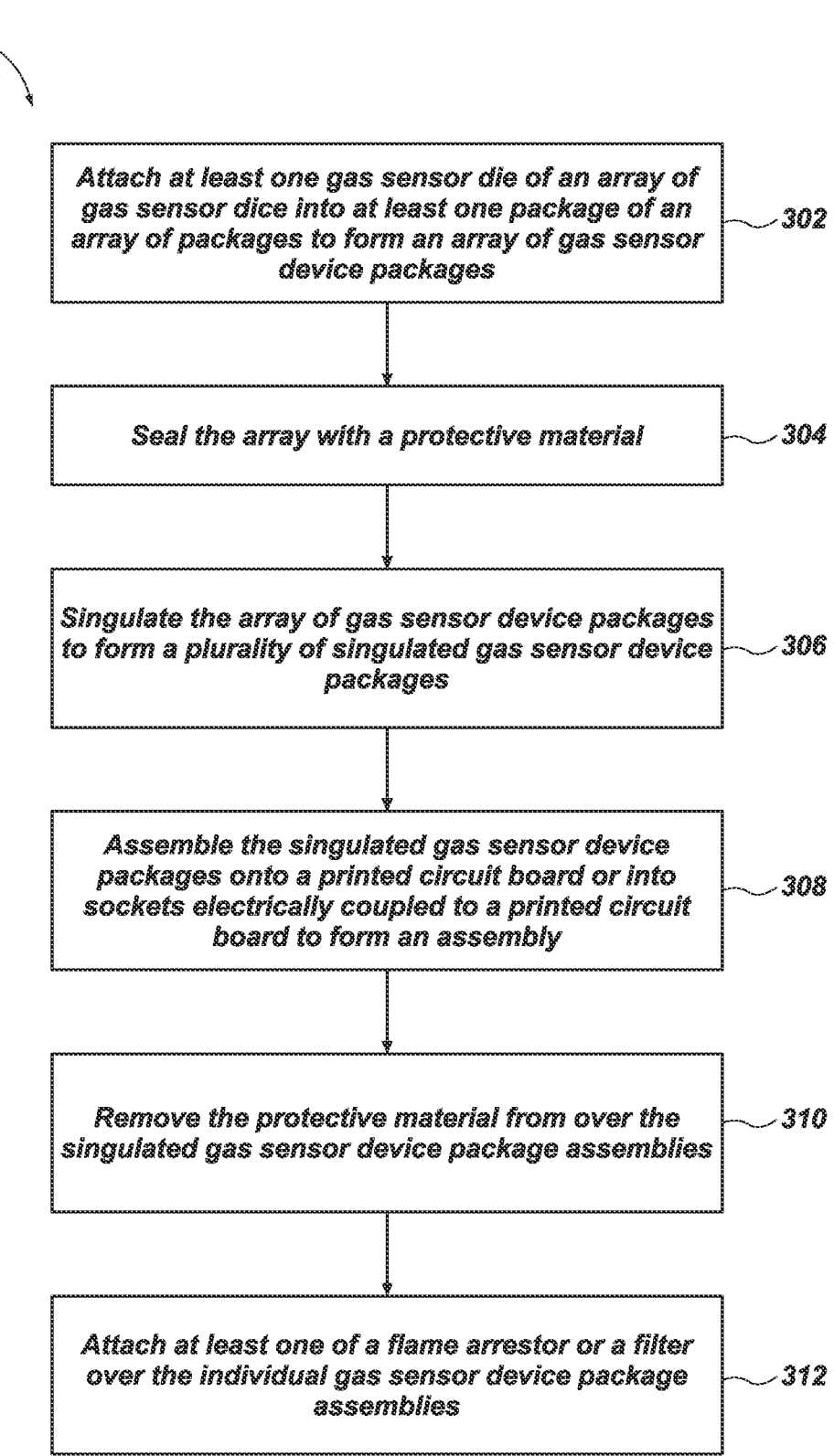

300

Attach at least one gas sensor die of an array of gas sensor dice into at least one package of an array of packages to form an array of gas sensor device packages — 302

Seal the array with a protective material — 304

Singulate the array of gas sensor device packages to form a plurality of singulated gas sensor device packages — 306

Assemble the singulated gas sensor device packages onto a printed circuit board or into sockets electrically coupled to a printed circuit board to form an assembly — 308

Remove the protective material from over the singulated gas sensor device package assemblies — 310

Attach at least one of a flame arrestor or a filter over the individual gas sensor device package assemblies — 312

FIG. 3A

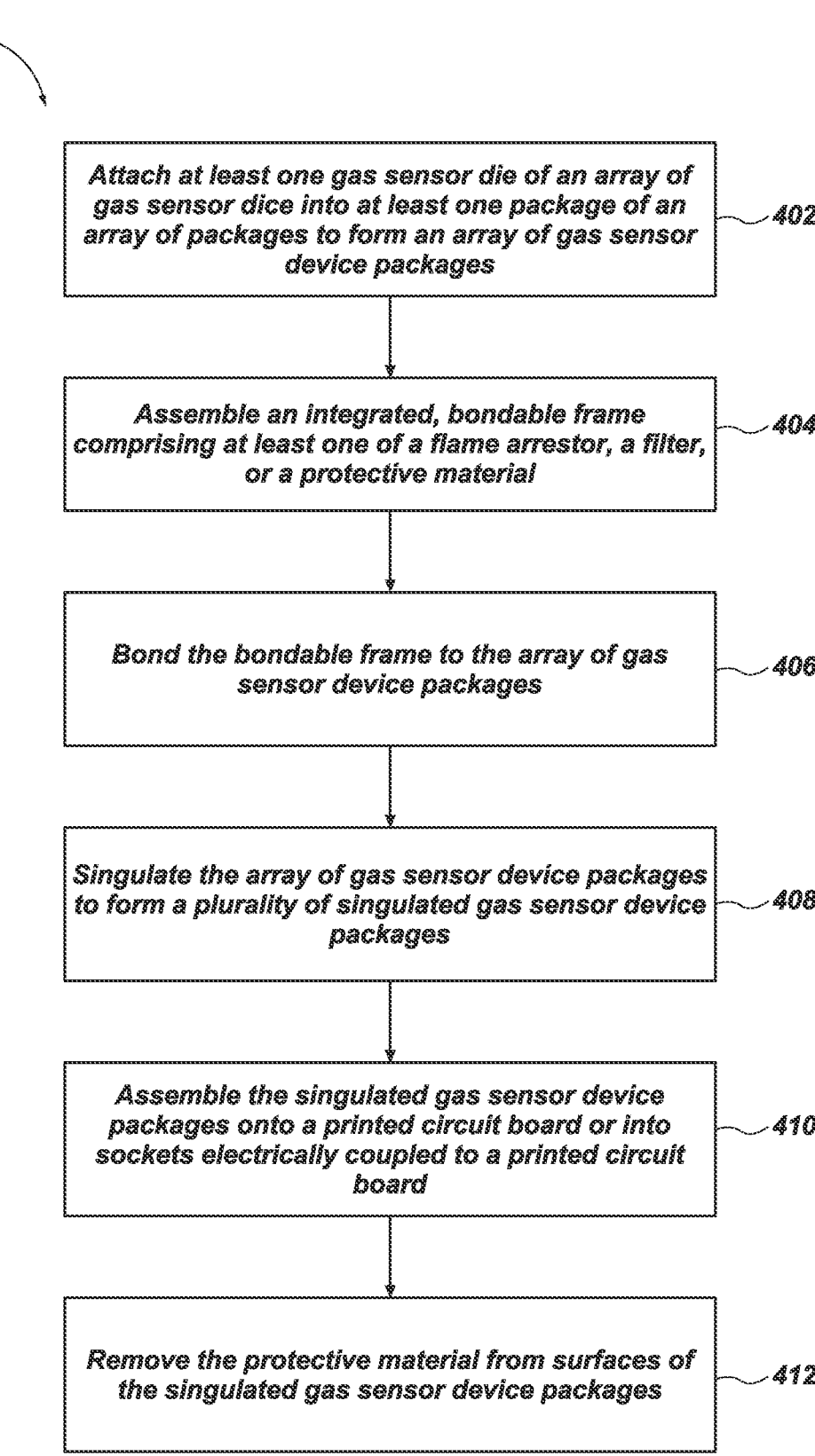

400

Attach at least one gas sensor die of an array of gas sensor dice into at least one package of an array of packages to form an array of gas sensor device packages ⟋402

Assemble an integrated, bondable frame comprising at least one of a flame arrestor, a filter, or a protective material ⟋404

Bond the bondable frame to the array of gas sensor device packages ⟋406

Singulate the array of gas sensor device packages to form a plurality of singulated gas sensor device packages ⟋408

Assemble the singulated gas sensor device packages onto a printed circuit board or into sockets electrically coupled to a printed circuit board ⟋410

Remove the protective material from surfaces of the singulated gas sensor device packages ⟋412

ARRAYS OF GAS SENSOR DEVICE PACKAGES, AND RELATED METHODS

CROSS-REFERENCE TO RELATED APPLICATIONS

This application is a national phase entry under 35 U.S.C. § 371 of International Patent Application PCT/US2021/071279, filed Aug. 25, 2021, designating the United States of America and published as International Patent Publication WO 2022/051743 A1 on Mar. 10, 2022, which claims the benefit under Article 8 of the Patent Cooperation Treaty to U.S. Patent Application Ser. No. 62/706,670, filed Sep. 2, 2020.

TECHNICAL FIELD

Embodiments of the disclosure relate generally to arrays of gas sensor device packages, and to related methods. More particularly, embodiments of the disclosure relate to arrays of gas sensor device packages including a plurality of individual gas sensor device packages, at least one gas sensor device package including at least one protective material over at least a portion thereof, and to related methods of fabricating the arrays of gas sensor device packages.

BACKGROUND

Electronic gas sensors are electrical devices that are exposed to air to accurately sense chemicals in the air. Such chemicals may include volatile organic compounds (VOCs), water, semi-volatile chemicals, volatile chemicals, aerosols, spores, and other chemicals. Gas sensors may include a variety of different heating elements. For example, micro-hotplates are used with catalytic and metal oxide semiconductor (MOS) coatings and also used to measure thermal conductivity of a sampled gas. A resonant gas sensor may include a heater used to desorb absorbed materials from the surface of the sensor. A gas pre-concentrator may have a heating element to affect the release of absorbed material. The gas sensors may be used to detect a presence of one or more gases, at least some of which may be flammable. However, in the presence of such heated components used for detection of gases, the flammable gases to which the gas sensor is exposed may ignite. To prevent the flames from travelling from the sensor to the location of the source of the flammable gases and causing an explosion, some sensors include a mechanism to arrest the flame. Accordingly, gas sensor device packages including gas sensors may include a so-called flame arrestor located in a region between the gas sensing component (e.g., the gas sensor) and the external environment to which the gas sensor is exposed.

The flame arrestor is formulated and configured to absorb the heat required for ignition and, therefore, may prevent an explosion. The flame arrestor of a conventional gas sensor device package may be located proximate the sensing material and may be configured to prevent an ignition source from escaping a cavity in which the gas sensor is disposed. The flame arrestor may allow gases to diffuse therethrough to the gas sensor, while preventing a potential flame (such as by quenching flames by absorbing heat from a potential ignition source) from propagating from the sensor cavity to the outside environment. However, use of a flame arrestor in a gas sensor may require separate manufacturing and assembly of the flame arrestor and the gas sensor device package, and may result in a large gap between the gas sensor and the flame arrestor. Further, the flame arrestor and gas sensor may become separated from each other after use and operation of the gas sensor (e.g., after multiple ignitions of a flammable gas), rendering the gas sensor unsafe for operation.

BRIEF SUMMARY

Embodiments disclosed herein include assemblies including gas sensor device packages, arrays of gas sensor device packages, and related methods of forming the gas sensor device packages and the arrays of gas sensor device packages. For example, in accordance with one embodiment, an array of gas sensor device packages comprises a plurality of gas sensor device packages, each gas sensor device package comprising a lead frame including bond pads and at least one gas sensor die in electrical communication with the bond pads, the gas sensor device packages each comprising at least one vent, and a protective covering over the plurality of gas sensor device packages.

Additional embodiments include an array of gas sensor device packages, the array comprising a plurality of gas sensor device packages within a package material, the package material defining a lead frame for each gas sensor device package of the plurality of gas sensor device packages, each gas sensor device package of the plurality of gas sensor device packages electrically connected to its respective lead frame, each gas sensor device package comprising at least one gas sensor die and a vent through which the gas sensor die is exposed, and a protective material over the vents of the plurality of gas sensor device packages.

In yet additional embodiments, a gas sensor device package comprises a lead frame, a thermoplastic material disposed around at least a portion of the lead frame and defining a cavity, at least one gas sensor die in the cavity at least partially defined by sidewalls and electrically connected to the lead frame, and a flame arrestor disposed over the sidewalls defining the cavity, at least a portion of the flame arrestor integral with the thermoplastic material of the sidewalls.

In further embodiments, a method of fabricating an array of gas sensor device packages comprises forming an array comprising a package material including a plurality of cavities defined by at least one of saw streets or sidewalls between adjacent cavities, electrically connecting at least one gas sensor die to the package material in at least some of the cavities, and forming at least one of a flame arrestor, at least one filter, or a protective material over the array to form an array of gas sensor device packages.

BRIEF DESCRIPTION OF THE DRAWINGS

FIG. 2A is a simplified flow diagram of a method of forming an array of gas sensor device packages, in accordance with embodiments of the disclosure;

FIG. 3A is a simplified flow diagram of a method of forming an array of gas sensor device packages, in accordance with embodiments of the disclosure;

FIG. 4A is a simplified flow diagram of a method of forming an array of gas sensor device packages, in accordance with embodiments of the disclosure;

DETAILED DESCRIPTION

Figure 1A:
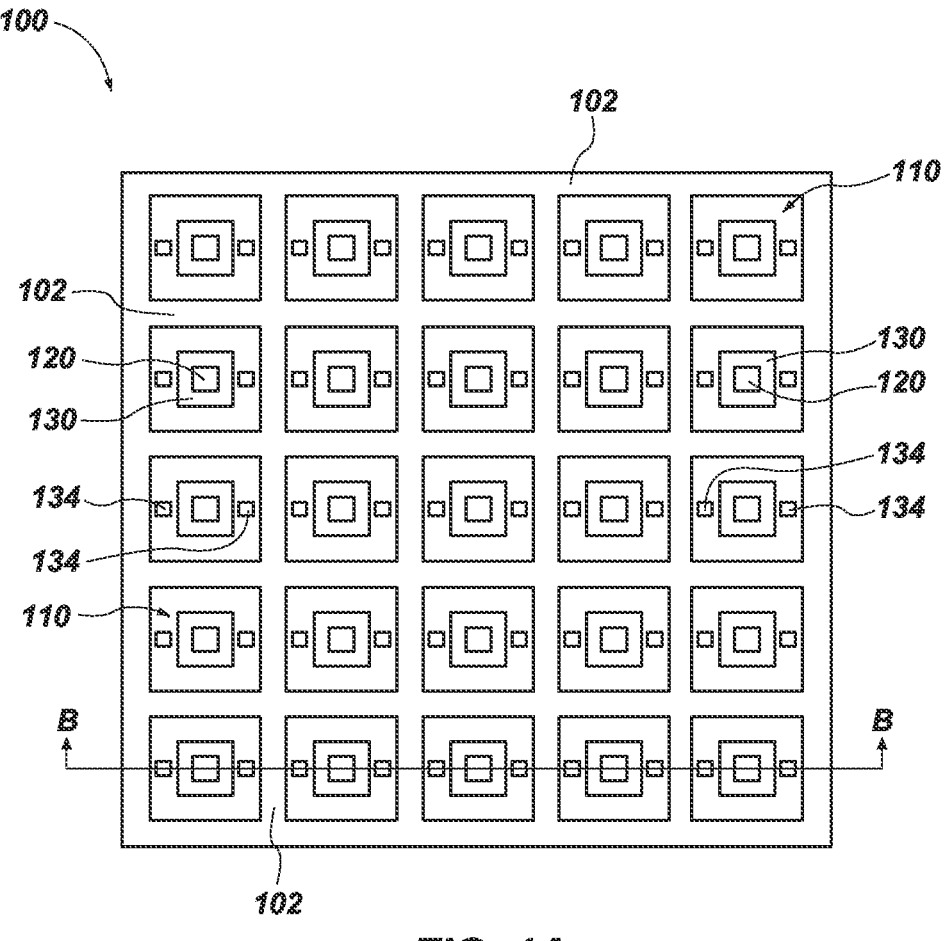
FIG. 1A is a simplified plan view of an array of gas sensor device packages, in accordance with embodiments of the disclosure.

Illustrations presented herein are not meant to be actual views of any particular material, component, or system, but are merely idealized representations that are employed to describe embodiments of the disclosure.

The following description provides specific details, such as material types, material thicknesses, and processing techniques in order to provide a thorough description of embodiments described herein. However, a person of ordinary skill in the art will understand that the embodiments disclosed herein may be practiced without employing these specific details. Indeed, the embodiments may be practiced in conjunction with conventional fabrication techniques employed in the industry.

As used herein, the term "vent" of a package (such as a gas sensor device package) means and includes one or more openings or apertures through which one or more components (e.g., die or dice) of the package are exposed to an external environment.

As used herein, the term "flame arrestor" means and includes a material or structure formulated and configured to allow a gas or other material to diffuse therethrough from an external environment to a sensor while preventing or substantially preventing a potential flame from propagating from the sensor to the external environment.

According to embodiments described herein, gas sensor device packages of an array of gas sensor device packages may be fabricated substantially simultaneously to form an array of packaged gas sensor devices. At least one gas sensor device package of the array of gas sensor device packages may comprise at least one gas sensor die formulated and configured to determine at least one property of a gas sample, such as at least one property of at least one analyte in the gas sample. At least one gas sensor device package of the array may further include other sensors (e.g., temperature sensors, humidity sensors, pressure sensors, etc.). At least one gas sensor device package (e.g., each gas sensor device package) may further include at least one protective material thereover, such as at least one of a temporary film, a cap, one or more filters, or a flame arrestor over the gas sensor device package, such as over vents of each of the gas sensor device packages. In some embodiments, the protective material overlies the array of gas sensor device packages. After the array of gas sensor device packages are formed, the array of gas sensor device packages may be singulated to form a plurality of singulated, packaged gas sensor device packages. Each singulated gas sensor device package may include at least one gas sensor die in the gas sensor device package, and may further include at least one of a flame arrestor, a lid, a filter, or a temporary film disposed over the gas sensor device package, such as over vents of each gas sensor device package. The individual gas sensor device packages may individually be assembled onto a printed circuit board (PCB) or another component, or disposed within a socket configured to be assembled onto a PCB or another component to form a gas sensor apparatus. Since the gas sensor device packages include the protective material thereover (e.g., over vents thereof) during fabrication of the gas sensor device package, the gas sensor device package (e.g., including one or more gas sensor dice within the gas sensor device package) may not be exposed to contaminants during singulation of the gas sensor device packages. In addition, the protective material may protect the gas sensor dice from contamination, such as from moisture, volatile organic compounds, dust, or other contaminants during attachment (e.g., surface mounting) of the singulated gas sensor device package onto a printed circuit board or to another component, or during washing of the gas sensor device package after surface mounting thereof onto the printed circuit board or other component. In some embodiments, the protective material may be removed after singulation of the array of gas sensor device packages and mounting of the singulated gas sensor device packages to a printed circuit board. In some such embodiments, the protective material may be referred to as a temporary protective material, such as a temporary film. In some embodiments, a protective material may remain in at least one gas sensor device package of the array after the array is singulated and after attaching the at least one gas sensor device package to a printed circuit board or other component. Such protective materials may be referred to as permanent protective materials and may comprise, for example, one or more filters, a flame arrestor, or a cap, as will be described herein.

FIG. 1A is a plan view an array 100 of gas sensor device packages 110, in accordance with embodiments of the disclosure. The array 100 may include an array of individual gas sensor device packages 110. Although FIG. 1A illustrates that the array 100 comprises 25 gas sensor device packages 110, the disclosure is not so limited and the array 100 may include fewer or more gas sensor device packages 110 (e.g., more than about 64, more than about 128, more than about 256, more than about 1,000, more than about 10,000, more than about 100,000, or more than about 1,000,000 gas sensor device packages 110).

Figure 1B:
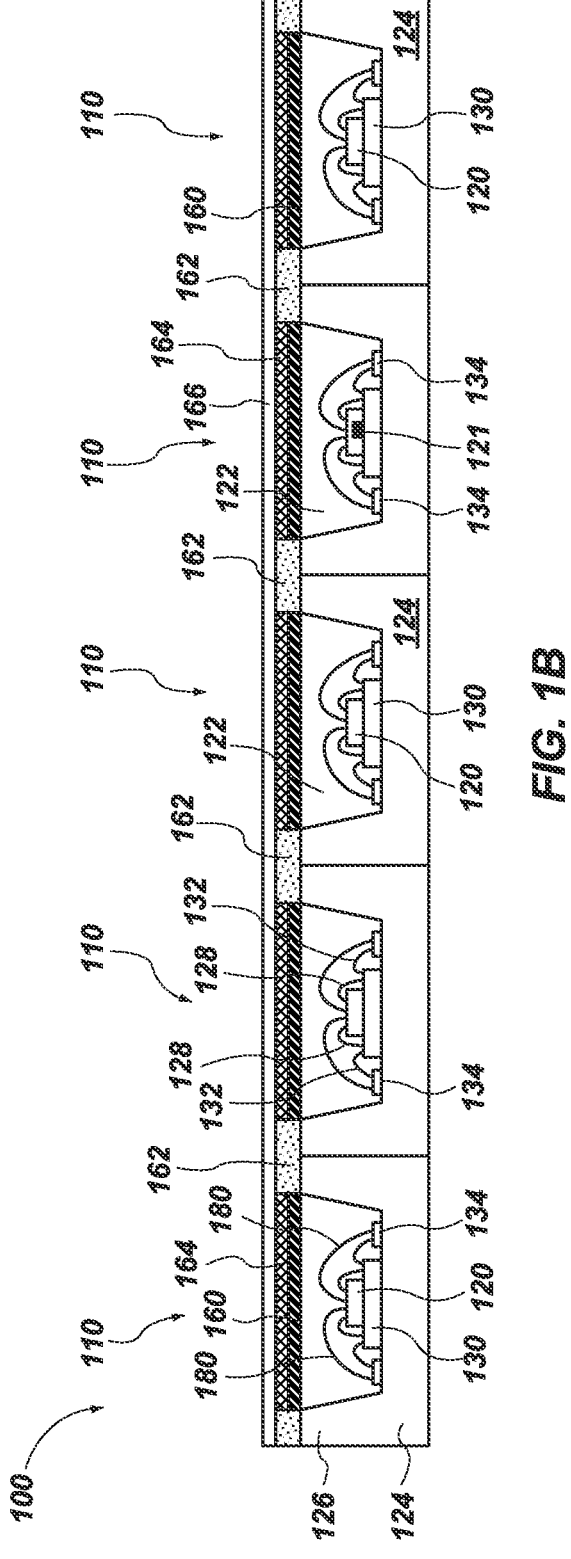
FIG. 1B is a simplified cross-sectional view of the array of FIG. 1A.

FIG. 1B is a simplified cross-sectional view of the array 100 taken along section line A-A of FIG. 1A. With reference to FIG. 1A and FIG. 1B, each gas sensor device package 110 may include one or more gas sensor dice 120 including one or more sensors configured to measure and detect at least one property of a gas sample. In some embodiments, the gas sensor dice 120 may be attached to a surface of the gas sensor device package 110 or onto another device (e.g., an application specific integrated circuit (ASIC) 130, as described below) that may be attached to the gas sensor device package 110.

The gas sensor device packages 110 may be isolated from each other by saw streets 102, which may also be referred to as die streets. As will be described herein, the array 100 may be configured to be cut (i.e., diced, singulated, etc.) along the saw streets 102 to singulate the gas sensor devices packages 110 and form individual gas sensor devices packages 110 to be assembled onto a printed circuit board (PCB) or other component to form a gas sensor assembly.

Figure 1C:
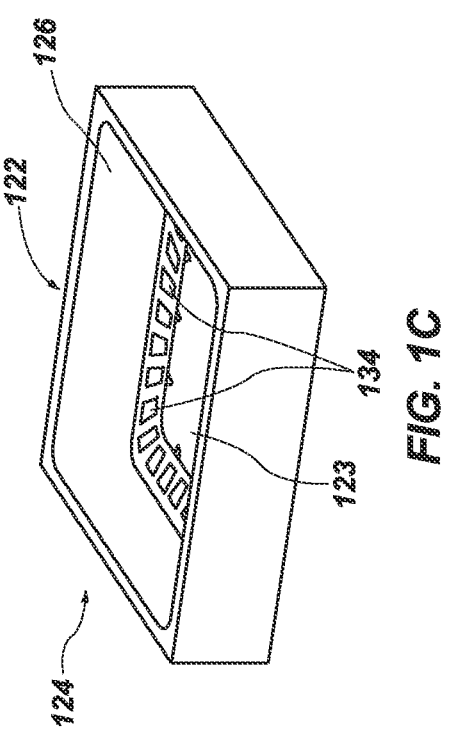
FIG. 1C is a simplified perspective view of single gas sensor device package of the array, in accordance with embodiments of the disclosure.

Each gas sensor device package 110 may include, for example, at least one gas sensor die 120 disposed in a cavity 122. The cavity 122 may be defined in a leadframe 124, which may comprise a premolded leadframe or a premolded package. FIG. 1C is a simplified perspective view of the leadframe 124 of a single gas sensor device package 110 (FIG. 1B) without the gas sensor die 120 or the ASIC 130 disposed in the cavity 122. Although FIG. 1C illustrates the leadframe 124 of only one gas sensor device package 110, it will be understood that the leadframe 124 includes an array of gas sensor device packages 110, as described and illustrated with reference to FIG. 1B. The leadframe 124 may include bond pads 134 for electrically connecting to the gas sensor die 120 (FIG. 1B), the ASIC 130 (FIG. 1C), or to other components. For example, bond wires 132, 180 (FIG. 1B) may be electrically connected to the bond pads 134 to place the gas sensor die 120 in electrical communication with the leadframe 124. The bond pads 134 may comprise strips of a metal, such as copper. The metal may be coated with another material, such as nickel, palladium, silver, gold, another metal, or combinations thereof. The bond pads 134 may extend from a location within the cavity 122 to a bottom side (which may also be referred to as a "back side") of the leadframe 124 to form terminals of the gas sensor device package 110 including the leadframe 124. The terminals of the gas sensor device package 110 located on the bottom side of the leadframe 124 may be configured to be connected to (e.g., electrically connected to) a printed circuit board or another component (e.g., a socket, which may be configured to be placed in electrical communication with a PCB) for forming a system including the gas sensor device package 110.

The leadframe 124 may further include a die attach pad 123 for electrically connecting the gas sensor die 120, the ASIC 130, or both to the leadframe 124 to form the gas sensor device package 110.

In some embodiments, at least a portion of the leadframe 124 comprises a thermoplastic material, a metal material, a ceramic material, or combinations thereof, which may surround and encapsulate at least portions of the bond pads 134 and/or the die attach pad 123. By way of non-limiting example, the leadframe 124 may include a ceramic material, a metal material (e.g., a metal can), a thermoplastic material, or combinations thereof. In some embodiments, the leadframe 124 comprises a thermoplastic material, such as, for example, a thermoplastic polymer (e.g., a polyphenyl ether (PPE) comprising low toluene, polyethylene, polypropylene, polyvinyl chloride (PVC), polystyrene, polytetrafluoroethylene (PTFE), acrylonitrile butadiene styrene, polyamide, etc.), a liquid crystal polymer (LCP) material (e.g., a material including fiber or spherical or naturally occurring fillers dispersed in a polymer matrix material), another material, or combinations thereof. The thermoplastic material may be disposed around and surround the electrical contacts of the leadframe 124, such as the bond pads 134 and/or the die attach pad 123.

In other embodiments, the leadframe 124 comprises a ceramic material (such as alumina ($Al_2O_3$)), or a metal material. In embodiments where the leadframe 124 comprises a ceramic material, surfaces of the leadframe 124 are metallized for forming the bond pads 134 and the die attach pad 123. In some such embodiments, an upper surface of the sidewalls 126 may be plated with a metal (e.g., nickel, gold, a combination thereof, etc.) to facilitate welding of another material thereon (e.g., a flame arrestor, a metal ring (e.g., a ring comprising an iron, nickel, cobalt, or combinations thereof), etc.). In embodiments where the leadframe 124 comprises a metal can, the metal can may include the die attach pad 123 and the bond pads 134 for forming electrical connections to the gas sensor die 120 and a printed circuit board. Use of a ceramic material or a metal material may reduce contamination of the gas sensor dice 120 and the gas sensor device package 110, since some plastic materials may inherently decompose or desorb VOCs during high temperature processing and may absorb moisture and VOCs during surface mounting of the gas sensor device package 110, which may reduce the sensitivity of the gas sensors of the gas sensor dice 120 during use and operation.

With reference again to FIG. 1B, the cavity 122 of at least one gas sensor device package 110 may be defined by sidewalls 126 extending from a base of the leadframe 124. The sidewalls 126 may comprise the same material as the leadframe 124, such as one or more of a ceramic material, a metal material (e.g., a metal can), a thermoplastic material, a polymer matrix material, or combinations thereof. In some embodiments, the sidewalls 126 comprise a thermoplastic material, such as, for example, a thermoplastic polymer (e.g., a polyphenyl ether (PPE) comprising low toluene, polyethylene, polypropylene, polyvinyl chloride (PVC), polystyrene, polytetrafluoroethylene (PTFE), acrylonitrile butadiene styrene, polyamide, etc.), a liquid crystal polymer (LCP) material (e.g., a material including fiber or spherical or naturally occurring fillers dispersed in a polymer matrix material), another material, or combinations thereof. In some embodiments, the sidewalls 126 comprise a liquid crystal polymer material. The material of the sidewalls 126 may exhibit a heat deflection temperature (i.e., a temperature at which a polymer or plastic deforms under a specified load, such as that specified in ASTM D648) (also referred to as a "heat distortion temperature") between about 120° C. and about 300° C., such as between about 120° C. and about 140° C., between about 140° C. and about 160° C., between about 160° C. and about 180° C., between about 180° C. and about 200° C., between about 200° C. and about 250° C., or between about 250° C. and about 300° C. In some embodiments, the heat deflection temperature of the sidewalls 126 is between about 140° C. and about 180° C. In some embodiments, a Vicat softening temperature (also referred to as a "Vicat hardness") of the material of the sidewalls 126 may be between about 150° C. and about 250° C., such as between about 150° C. and about 175° C., between about 175° C. and about 200° C., between about 200° C. and about 225° C., or between about 225° C. and about 250° C.

The gas sensor dice 120 may each include one or more bond pads 121 (one of which is illustrated in FIG. 1B) formulated and configured to determine one or more properties of a gas sample, such as a presence of an analyte of interest, a concentration of an analyte of interest in the gas sample, a thermal conductivity of the gas sample, a composition of the gas sample, another property of the gas sample, or combinations thereof. In some embodiments, at least one gas sensor die 120 may include one or more of a so-called metal oxide semiconductor (MOS), a resonant sensor, a thermal conductivity sensor, a catalytic sensor, an optical sensor, an infrared (IR) sensor, an electrochemical sensor, another sensor, and combinations thereof.

In some embodiments, at least one sensor of one or more gas sensor dice 120 may include a MOS sensor, the MOS sensor including a heater and a hotplate including (e.g., consisting of) a base material having a temperature controlled by a heater, and a metal oxide semiconductor sensing material disposed over the hotplate. An interdigitated electrode (IDE) may be disposed over the hotplate and in electrical communication with the metal oxide semiconductor sensing material. A resistivity of the metal oxide semiconductor sensing material may be dependent upon a property of the gas sample (e.g., a presence and/or a concentration of one or more analytes in the gas sample). The IDE may be configured to measure the resistance across the metal oxide semiconductor material to determine at least one property of the gas sample.

In some embodiments, at least one sensor of one or more gas sensor dice 120 may include a resonant sensor. The resonant sensor may include, for example, a microcantilever suspended over a cavity. A coating, such as a polymer coating, formulated and configured to interact with at least one analyte of interest, may overlie the microcantilever. The resonant sensor may be configured to determine at least one property of the gas sample, such as viscous damping, which may be used to determine a presence of an analyte of interest, a concentration thereof, another property, or combinations thereof.

In some embodiments, at least one sensor of one or more gas sensor dice 120 may include a thermal conductivity sensor, a catalytic microhotplate sensor (including a catalytic sensing material, such as, for example, platinum, palladium, etc.), or another sensor configured to determine one or more properties of the gas sample.

With continued reference to FIG. 1B, in some embodiments, the gas sensor die 120 may be electrically coupled to an application specific integrated circuit (ASIC) 130 with one or more bond wires 128. The bond wires 128 may electrically connect bond pads of the gas sensor die 120 to bond pads of the ASIC 130. The ASIC 130 may be electrically coupled to bond pads 134 of the leadframe 124 with one or more bond wires 132. In some embodiments, each gas sensor die 120 is directly electrically coupled to the bond pads 134 of the leadframe 124 (and may not be directly coupled to the ASIC 130 with the bond wires 132), such as with bond wires 180 electrically connecting the gas sensor dice 120 to the leadframe 124. The bond wires 128, 132, 180 are not illustrated in FIG. 1A for clarity.

The array 100 may include at least one protective material overlying the gas sensor device packages 110. The at least one protective material may include one or more of a flame arrestor 160, a filter 164, and a protective film 166 overlying the gas sensor device packages 110. The at least one protective material may seal the gas sensor device packages 110 during dicing and assembly of the gas sensor device packages 110 and substantially prevent contaminants (e.g., dust, water, etc.) from contacting the gas sensor dice 120 of the gas sensor device packages 110. As will be described herein, the protective material may include at least one opening over one or more of the gas sensor device packages 110, which opening may also be referred to herein as a vent or an aperture. Accordingly, the gas sensor device packages 110 may include a vent (e.g., one or more openings or apertures) through which the gas sensor dice 120 are exposed. The protective material may be referred to herein as a "vent covering."

In some embodiments, the filter 164 may overlie the flame arrestor 160 and the protective film 166 overlies the filter 164. However, the disclosure is not so limited and, in other embodiments, the flame arrestor 160 may overlie the filter 164, for example. Similarly, although FIG. 1B illustrates the flame arrestor 160, the filter 164, and the protective film 166, in some embodiments, the array 100 may not include the flame arrestor 160 and may include, for example, the filter 164 and the protective film 166 over the filter 164. In other embodiments, the array 100 may not include the filter 164 and may include the protective film 166 directly over the flame arrestor 160. In some embodiments, such as embodiments not including the flame arrestor 160 or the filter 164, the protective film 166 may overlie the array 100 of gas sensor device packages 110 and may protect the gas sensor dice 120 from contaminants during singulation of the array 100 and during assembly of the singulated gas sensor device packages 110 onto, for example, printed circuit boards.

The flame arrestor 160 may include a material formulated and configured to hinder or substantially prevent a flammable gas from being ignited outside of the gas sensor device packages 110 during use and operation thereof. In other words, the flame arrestor 160 may be formulated and configured to substantially prevent a potential flame from propagating from the cavity 122 to the outside environment. In some embodiments, the flame arrestor 160 comprises a material formulated and configured to absorb heat required for combustion of flammable gases proximate the gas sensor device package 110. In some embodiments, the flame arrestor 160 comprises a wire gauze, a perforated plate, a sintered plate comprising a sintered ceramic material, crimped metal, a tightly woven twill dutch weave comprising stainless steel, or combinations thereof. Although FIG. 1B illustrates the flame arrestor 160 over the vent, the disclosure is not so limited. For example, as will be described herein (such as with reference to FIG. 4L), the flame arrestor 160 may be located below the vent.

The flame arrestor 160 may include, for example, a metal mesh comprising stainless steel (e.g., 316 stainless steel (including about 18% chromium and about 8% nickel), 304 stainless steel (including about 16% chromium, 10% nickel, and about 2% molybdenum), etc.), titanium, aluminum, carbon steel, iron, copper, another material, or combinations thereof. In some embodiments, the flame arrestor 160 comprises a magnetic material, such as 304 stainless steel.

As will be described herein, at least one of the flame arrestor 160, the filter 164, and the protective film 166 may be placed over one or more individual gas sensor device packages 110 in the array 100 substantially simultaneously. In some embodiments, each of the flame arrestor 160, the filter 164, and the protective film 166 comprises a continuous and unitary body. For example, even though the flame arrestor 160 may comprise a porous material or a wire mesh material, in some embodiments, the flame arrestor 160 over one gas sensor device package 110 may not be separate and distinct from the flame arrestor 160 over other gas sensor device packages 110.

As will be described herein, the flame arrestor 160 may be bonded to the array 100, such as by thermal bonding, swaging, welding, with an epoxy, with an adhesive, by another method, or combinations thereof. The flame arrestor 160 may be bonded to the individual gas sensor device packages 110 at bonding locations 162. The bonding locations 162 may be where the sidewalls 126 of the leadframe 124 intersect the flame arrestor 160. At the bonding locations 162, the flame arrestor 160 may be disposed within and surrounded by the material of the sidewalls 126 (e.g., a thermoplastic material). In some embodiments, where the flame arrestor 160 comprises a metal mesh, the material of the sidewall 126 material may substantially surround the flame arrestor 160. Accordingly, the flame arrestor 160 may be bonded to the gas sensor device packages 110 at locations defining a periphery of each of the gas sensor device packages 110 and may further be bonded to the array 100 at the saw streets 102.

The filter 164 may include a material formulated and configured to filter dust, dirt, gases, humidity, other contaminants or materials from entering the cavity 122 and contacting, for example, the gas sensor die 120. In some embodiments, the filter 164 comprises two layers, a first layer configured to filter dust, dirt, or other contaminants, and a second layer configured to filter one or more gases, humidity, or other materials. In some embodiments, the filter 164 may be removable from surfaces of the array 100. In some such embodiments, the filter 164 may be disposed over the flame arrestor 160. The filter 164 may be configured to remain over each gas sensor device package 110 after singulation thereof and may be referred to as a permanent protective material. In some embodiments, the filter 164 comprises a first portion comprising polytetrafluoroethylene (PTFE) and a second portion comprising charcoal.

In some embodiments, where the filter 164 is located below the flame arrestor 160 (or where the array 100 does not include the flame arrestor 160), the filter 164 may overlie and contact the sidewalls 126 of the package material 124. In some such embodiments, the filter 164 may be bonded to the array, such as by thermal bonding, swaging, welding, with an epoxy, with an adhesive, by another method, or combinations thereof. The filter 164 may be bonded to the individual gas sensor device packages 110 at bonding locations 162. Accordingly, in some such embodiments, the filter 164 may be bonded to the gas sensor device packages 110 at locations defining a periphery of each of the gas sensor device packages 110 and may further be bonded to the array 100 at the saw streets 102.

The protective film 166 may overlie array 100, such as the flame arrestor 160, the filter 164, and the bonding locations 162 over the array 100. The protective film 166 may comprise a film, a tape, a lid, a self-developing photoresist material (e.g., a nitrocellulose material), a polymer material, such as, for example, a polyimide, polyethylene, polyurethane, another material, or combinations thereof. In embodiments, such as where the protective film 166 comprises nitrocellulose, the protective film 166 may comprise a self-developing resist material formulated and configured to decompose responsive to exposure to ultraviolet light. For example, where the protective film 166 comprises nitrocellulose, the nitrocellulose may decompose into carbon dioxide and nitrogen responsive to exposure to ultraviolet light. The carbon dioxide and nitrogen may not damage the components of the gas sensor dice 120. In some embodiments, the protective film 166 is ink marked to provide traceability to one or more of the individual gas sensor device packages 110.

Although the protective film 166 has been described and illustrated as comprising a substantially planar material overlying the cavity 122 of each gas sensor device package 110 of the array 100, the disclosure is not so limited. In other embodiments, and as will be described herein, the protective film 166 may comprise a lid disposed over at least some of the gas sensor device packages 110 of the array 100.

After the protective film 166 (or lid) is placed over the array 100, the array 100 may be cut at the saw streets 102 to singulate the gas sensor device packages 110 into individual gas sensor device packages 110. Accordingly, at least one of the protective film 166 (or the lid), the filter 164, or the flame arrestor 160 may protect the gas sensor dice 120 in the gas sensor device packages 110 from contamination during singulation of the gas sensor device packages 110. In addition, the protective material may protect the gas sensor dice 120 from moisture during, for example, surface mounting the individual gas sensor device packages to a printed circuit board.

In some embodiments, a height of the bond wires 128, 132, 180, defined as a distance between a surface of the gas sensor die 120 and an uppermost portion of the bond wires 128, 132, 180 located distal from the surface of the gas sensor die 120, may be less than about 50 μm, such as less than about 40 μm. Such a reduced height may reduce a distance between a top surface of the gas sensor die 120 and a bottom surface of a flame arrestor 160 associated with the gas sensor device package 110. In some embodiments, the height is reduced by reverse bonding, folded bond technology, or a combination thereof. For example, in some embodiments, a ball may be formed over an upper surface of a conductive pad of the gas sensor die 120. A second end of the bond wire 128 may be attached to the bond pads 134 of the leadframe 124 to form a wedge bond. In some embodiments, a conductive (e.g., a gold) ball is formed over the bond pad of the gas sensor die 120. The first end of the wire is then ball bonded to the bond pads 134 and the second end is reverse bonded to the top of the conductive ball. In some embodiments, a conductive ball may be bonded to the leadframe 124 and the bond wires 128, 132, 180 may be bent over to the conductive ball and the second end of the wire is then wedge bonded to the bond pads 134 of the lead frame.

Although FIG. 1A through FIG. 1C have been described and illustrated as including the gas sensor die 120 in electrical communication with the ASIC 130 via bond wires 128 and the ASIC 130 in electrical communication with the leadframe 124 via bond wires 132, the disclosure is not so limited. In other embodiments, and as described with reference to FIG. 1D through FIG. 1G, the gas sensor die 120, the ASIC 130 (if present), or both may be in electrical communication with the leadframe 124 by other means. As one non-limiting example, in some embodiments, the gas sensor die 120 and the ASIC 130 may each be directly bonded to the bond pads 134 of the leadframe 124. In some embodiments, the gas sensor device package 110 does not include the ASIC 130 and the gas sensor dice 120 are in direct electrical communication with the leadframe 124.

Figure 1D:
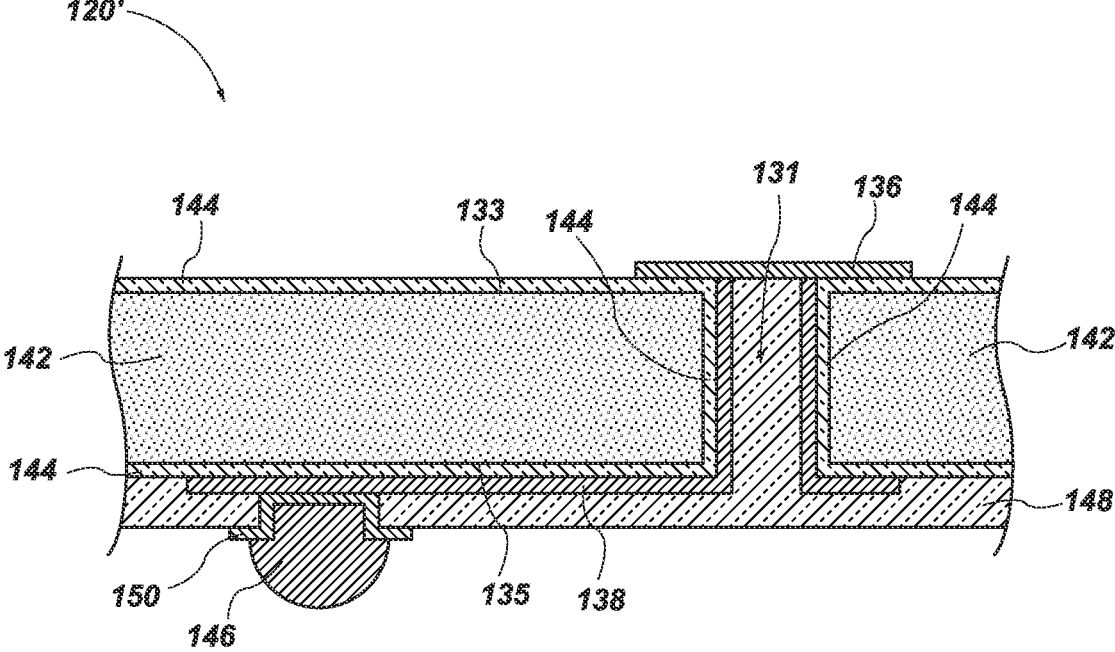
FIG. 1D is a simplified cross-sectional view of a gas sensor die including a through silicon via electrically connected to a conductive bump by means of a redistribution layer, in accordance with embodiments of the disclosure.

FIG. 1D is a simplified cross-sectional view of a gas sensor die 120' including one or more through silicon vias (TSVs) 131 configured to electrically connect the gas sensor die 120' to another component (e.g., an ASIC die 130 (FIG. 1B) or the leadframe 124 (FIG. 1C)). The through silicon via 131 may be electrically connected to a conductive pad 136 on a top surface 133 of the gas sensor die 120'. The conductive pad 136 may be in electrical communication with one or more components of the gas sensor die 120', such as with one or more gas sensing components thereof. The gas sensor die 120' may include a conductive material 138 on a back side 135 thereof. The back side 135 may also be referred to herein as the bottom of the gas sensor die 120'. The conductive material 138 may be in electrical communication with the conductive pad 136 by means of the through silicon via 131 extending through a substrate 142 of the gas sensor die 120'. The conductive material 138 may extend through the substrate 142 and line sidewalls of the through silicon via 131. An insulative material 144 may line sidewalls of the through silicon via 131. Accordingly, the conductive pad 136 and the conductive material 138 may be electrically conductive material isolated from the substrate 142 by the insulative material 144 lining sidewalls of the conductive material 138 within the through silicon via 131 and at least some surfaces of the substrate 142.

The conductive material 138 on the back side 135 may be in electrical communication with a conductive bump 146 in electrical communication with a conductive seed material 150 in electrical communication with the conductive material 138. A passivation material 148 may provide electrical insulation between the conductive material 138 and other components of the gas sensor die 120' or associated gas sensor device package. Since the conductive material 138 extends across the back side 135 and forms an electrical connection between the conductive pad 136 and the conductive bump 146, which are laterally offset from one another, the conductive material 138 may be referred to as a redistribution line.

The conductive bump 146 may be configured to electrically connect the gas sensor die 120' to another component (e.g., such as the ASIC die 130 (FIG. 1C), the leadframe 124 (FIG. 1B)). In some embodiments, the conductive bump 146 may be configured to be soldered to the leadframe 124. Soldering of the conductive bumps 146 to the leadframe 124 may be referred to as fluxless flip chip bonding of the conductive bumps 146 to the leadframe 124.

With continued reference to FIG. 1D, in some embodiments, portions of the back side 135 gas sensor die 120' may be coated with a solderable metal, such as tin, gold, or a combination thereof. In some embodiments, titanium may be disposed (e.g., sputtered, grown, etc.) on back side 135 of the gas sensor die 120' to form an adhesion layer over a silicon surface of the gas sensor die 120'. Copper may be disposed over the titanium adhesion layer and gold may be disposed over the copper to form a composite layer comprising titanium, copper, and gold on the back side of the gas sensor die 120'. The composite layer may be formed through a shadow mask covering (masking) portions of a package array comprising a plurality of the gas sensor dice 120'. In some embodiments, saw streets 102 of the package array may be covered with the shadow mask such that the composite layer is not formed on the saw streets. Since the saw streets 102 do not include the composite layer, the package array may be diced to singulate the gas sensor dice 120'. The conductive bumps 146 of the singulated gas sensor dice 120' may be soldered to the package material 124.

Although FIG. 1D illustrates the conductive pad 136 of the gas sensor die 120' and conductive bump 146 as being laterally offset from one another, in other embodiments, the conductive pad 136 and the conductive bump 146 may be laterally aligned with one another.

In other embodiments, the gas sensor die 120 may not include the through silicon vias 131, as described with reference to FIG. 1D. For example, referring to FIG. 1E, a gas sensor device package 110' may include a gas sensor die 120 overlying an ASIC 130. Bond wires 180 may be electrically connect bond pads of the gas sensor die 120 with bond pads 134 of the leadframe 124. The ASIC 130 may include conductive bumps (e.g., conductive balls) 137 electrically connected to the leadframe 124 (such as to bond pads 134 of the leadframe 124), such as by flip chip bonding the ASIC 130 to the leadframe 124. Accordingly, the gas sensor die 120 and the ASIC 130 may be in electrical communication with the printed leadframe 124. In some embodiments, the gas sensor die 120 and the ASIC 130 are in electrical communication with each other through the electrical connections to the leadframe 124. Although FIG. 1E illustrates the leadframe 124 and does not show the sidewalls 126, it will be understood that the leadframe 124 includes sidewalls 126 to define a cavity 122, as described above with reference to FIG. 1B.

In yet other embodiments, the gas sensor die 120 and the ASIC 130 (if present) may be electrically connected to a redistribution layer. For example, with reference to FIG. 1F, a gas sensor device package 110" may include at least one gas sensor die 120 and an ASIC 130. Bond pads 121 of the gas sensor die 120 may be in electrical communication with a redistribution layer 140, which may be in electrical communication with bond pads (e.g., the bond pads 134 (FIG. 1C)) of the package material 124. Accordingly, the gas sensor die 120 may be in electrical communication with the leadframe 124 (package material) through the redistribution layer 140. The redistribution layer 140 may form an electrical connection between the bond pads 121 of the gas sensor die 120 and the bond pads of the leadframe 124 (package material), even though the bond pads 121 and the bond pads 134 (FIG. 1C) of the leadframe 124 are not laterally aligned with one another. The gas sensor device package 110" may further include another redistribution layer 141 in electrical communication with bond pads 139 of the ASIC 130 and with bond pads 134 of the leadframe 124. Accordingly, the ASIC 130 may be in electrical communication with the package material 124 through the redistribution layer 141. The redistribution layer 141 may form an electrical connection between the bond pads 134 of the ASIC 130 and the bond pads of the leadframe 124, even though the bond pads 134 and the bond pads 134 of the leadframe 124 are not laterally aligned with one another.

Figure 1E:
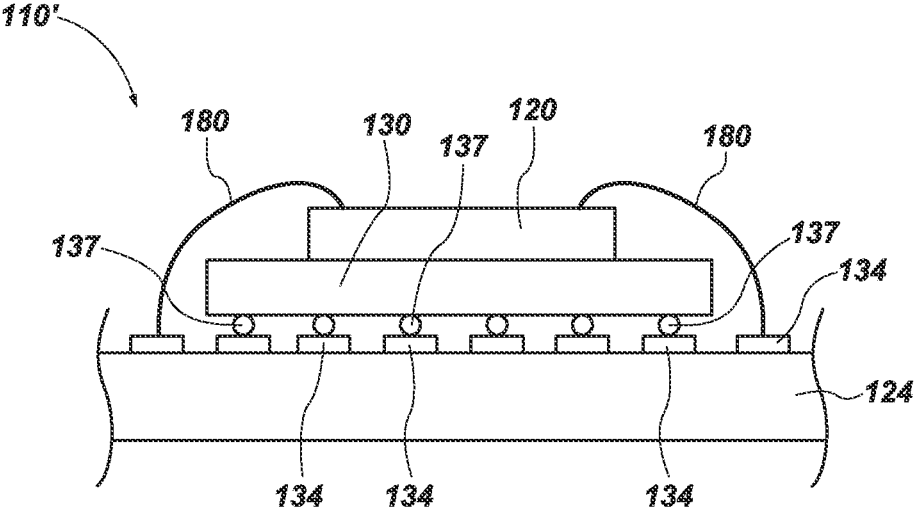
FIG. 1E is a simplified cross-sectional view of a gas sensor device package including a gas sensor die and an ASIC bonded to a package material, in accordance with embodiments of the disclosure.
Figure 1F:
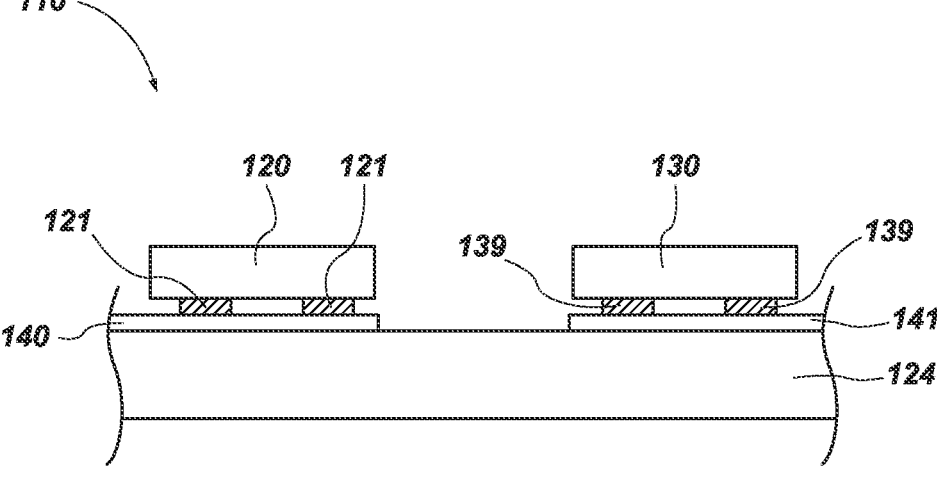
FIG. 1F is a simplified cross-sectional view of a gas sensor device package including redistribution layers between a package material and a gas sensor die and an ASIC, in accordance with embodiments of the disclosure.

Although FIG. 1B, FIG. 1D, FIG. 1E, and FIG. 1F have been described and illustrated as including the gas sensor die 120, 120' in electrical communication with the ASIC 130, and the ASIC 130 in electrical communication with the package material 124, the disclosure is not so limited. In other embodiments, the gas sensor device packages 110, 110', 110" may not include the ASIC 130 and the gas sensor dice 120, 120' may be in direct electrical communication with the leadframe 124, such as through the through silicon vias 131 (FIG. 1D) and conductive bumps 146 (FIG. 1D) and/or conductive pads 136 (FIG. 1D), or bond wires 180 (FIG. 1E).

Figure 1G:
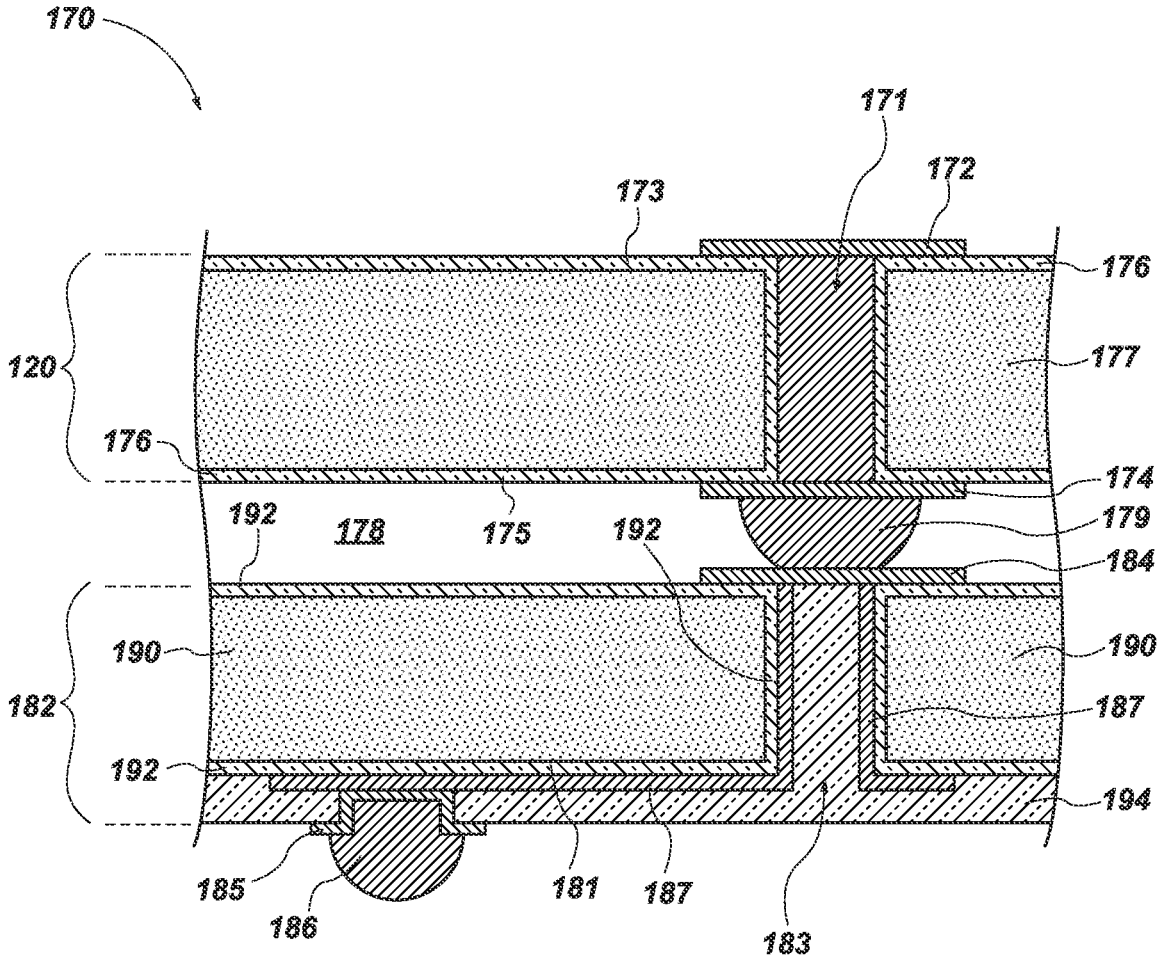
FIG. 1G is a simplified cross-sectional view of an assembly for electrically coupling a gas sensor die to a redistribution substrate, in accordance with embodiments of the disclosure.

FIG. 1G is a simplified cross-sectional view of an assembly 170 for electrically coupling a gas sensor die 120 to a redistribution substrate 182, in accordance with embodiments of the disclosure. The redistribution substrate 182 may be configured to redistribute electrical circuitry from one lateral position to another and may also be referred to herein as an interposer. The redistribution substrate 182 may comprise a substrate 190, which may include a semiconductive material, a ceramic material, or a polymer material. In some embodiments, the redistribution substrate 182 can accommodate a plurality of dice (e.g., other gas sensor dice 120, electronics dice, communication dice, calibration source dice, memory dice, etc.) and can include interconnections between the dice as well as connections to the bottom surface of the redistribution substrate 182 to conductive balls 186.

The gas sensor die 120 may include a conductive pad 172 located on a front side 173 of the gas sensor die 120, which may be in electrical communication with one or more components of the gas sensor die 120, such as one or more gas sensing components. Although FIG. 1G illustrates only one conductive pad 172, it will be understood that the gas sensor die 120 may include a plurality of conductive pads 172. The conductive pad 172 may be in electrical communication with another conductive pad 174 by means of a through substrate via 171 extending through a substrate 177 of the gas sensor die 120. The substrate 177 may comprise a semiconductor material, a ceramic material, a polymer material, or another material.

The through substrate via 171 may comprise an electrically conductive material. The conductive pad 174 may be located on a back side 175 of the gas sensor die 120. In some embodiments, an insulative material 176, such as silicon oxide, silicon nitride, or another electrically insulative material may electrically isolate the conductive pads 172, 174 from the substrate 177.

A conductive bump 179 may be in electrical communication with the conductive pad 174 and may be in electrical communication with a conductive pad 184 of the redistribution substrate 182. The conductive pad 184 may be in electrical communication with a through substrate via 183 comprising an electrically conductive material. The through substrate via 183 may include an electrically conductive material 187 on sidewalls of the through substrate via 183. The through substrate via 183 may be in electrical communication with a conductive pad 185 on a back side 181 of the redistribution substrate 182 by means of the electrically conductive material 187, which may extend over a surface of the back side 181 of the redistribution substrate 182. The conductive pad 185 may be in electrical communication with a conductive ball 186. The conductive ball 186 may be laterally offset from the through substrate via 183.

In some embodiments, an insulative material 192 (e.g., a dielectric material) may electrically isolate the conductive material 187 from the substrate 190. Another insulative material 194 may overlie surfaces of the electrically conductive material 187 and may fill the through substrate via 183.

In some embodiments, a volume 178 between the gas sensor die 120 and the redistribution substrate 182 may be filled with an electrically insulative material. In other embodiments, the volume 178 may be filled with air.

Although FIG. 1B through FIG. 1G have illustrated specific methods of electrically coupling the gas sensor dice 120, 120' to the package material 124, the disclosure is not so limited and the gas sensor dice 120, 120' may be electrically coupled to the package material 124 by other methods.

FIG. 2A is a simplified flow diagram of a method 200 of forming an array of gas sensor device packages, in accordance with embodiments of the disclosure. The method 200 includes act 202 including attaching at least one gas sensor die of an array of gas sensor dice into at least one package of an array of packages to form an array of gas sensor device packages; act 204 including bonding at least one of a flame arrestor or at least one filter over the array of gas sensor device packages; act 206 including sealing at least one of the flame arrestor or the at least one filter to the array of gas sensor device packages with a protective material or lid; act 208 including singulating the array of gas sensor device packages to form a plurality of singulated gas sensor device packages; act 210 including assembling the singulated gas sensor device packages onto a printed circuit board or into sockets electrically coupled to a printed circuit board; and act 212 including forming an opening over a surface of the singulated gas sensor device packages.

Act 202 includes attaching at least one gas sensor die of an array of gas sensor dice into at least one package of an array of packages to form an array of gas sensor device packages. The package array may comprise, for example, a leadframe including electrical connections (e.g., the bond pads 134 and the die attach pads 123 described above with reference to the leadframe 124 of FIG. 1C). With reference to FIG. 1B, act 202 may include wirebonding the gas sensor dice 120 to the leadframe 124. In some embodiments, conductive pads of the gas sensor die 120 may be wirebonded to the bond pads 134 (FIG. 1C) of the leadframe 124 to form an array of gas sensor device packages 110, each gas sensor device package 110 of the array 100 of gas sensor device packages 110 comprising at least a gas sensor die 120 bonded to a location of the leadframe 124.

The gas sensor dice 120 may be attached to the leadframe 124 with, for example, wire bonds, conductive bumps, a redistribution substrate, or other method, as described above with reference to FIG. 1D through FIG. 1G. Accordingly, act 202 includes electrically coupling the gas sensor dice 120 to the leadframe 124 of the package array.

Act 204 may include bonding at least one of a flame arrestor or at least one filter over the array of gas sensor device packages. The flame arrestor and the filter may have substantially the same cross-sectional size and shape as the array 100 of gas sensor device packages 110 (FIG. 1A). In some such embodiments, the flame arrestor and the filter may be formed to have a size and shape corresponding to the size and shape of the array 100 of gas sensor device packages 110. In other words, the array 100 may include a plurality of gas sensor device packages 110 and the flame arrestor and the filter may be sized and shaped to overlie the plurality of gas sensor device packages 110. The flame arrestor may comprise a unitary (e.g., continuous) body extending over the plurality of gas sensor device packages 110. The flame arrestor may comprise the same materials described above with reference to the flame arrestor 160 (FIG. 1B).

In some embodiments, at least one filter may be bonded over the flame arrestor. The filter may include a material formulated and configured to remove (e.g., filter) dust, dirt, or other contaminants, a material for filtering moisture, a material formulated and configured filter one or more gases (e.g., hydrogen sulfide, carbon monoxide, ethanol, and/or other materials that may damage (e.g., poison) sensing materials of the gas sensor die 120), or combinations thereof. In some embodiments, the filter comprises one or more layers configured to filter one or more gases, dust, water, or combinations thereof. By way of non-limiting example, the filter may comprise a first layer configured to remove dust (e.g., a dust cover), a second layer configured to remove moisture, and a third layer configured to remove one or more gases. In some embodiments, the first layer, the second layer, and the third layer comprise a unitary filter structure. In other embodiments, the first layer, the second layer, and the third layer are separate and distinct and may be bonded over the flame arrestor separately.

Figures 2B, 2C:
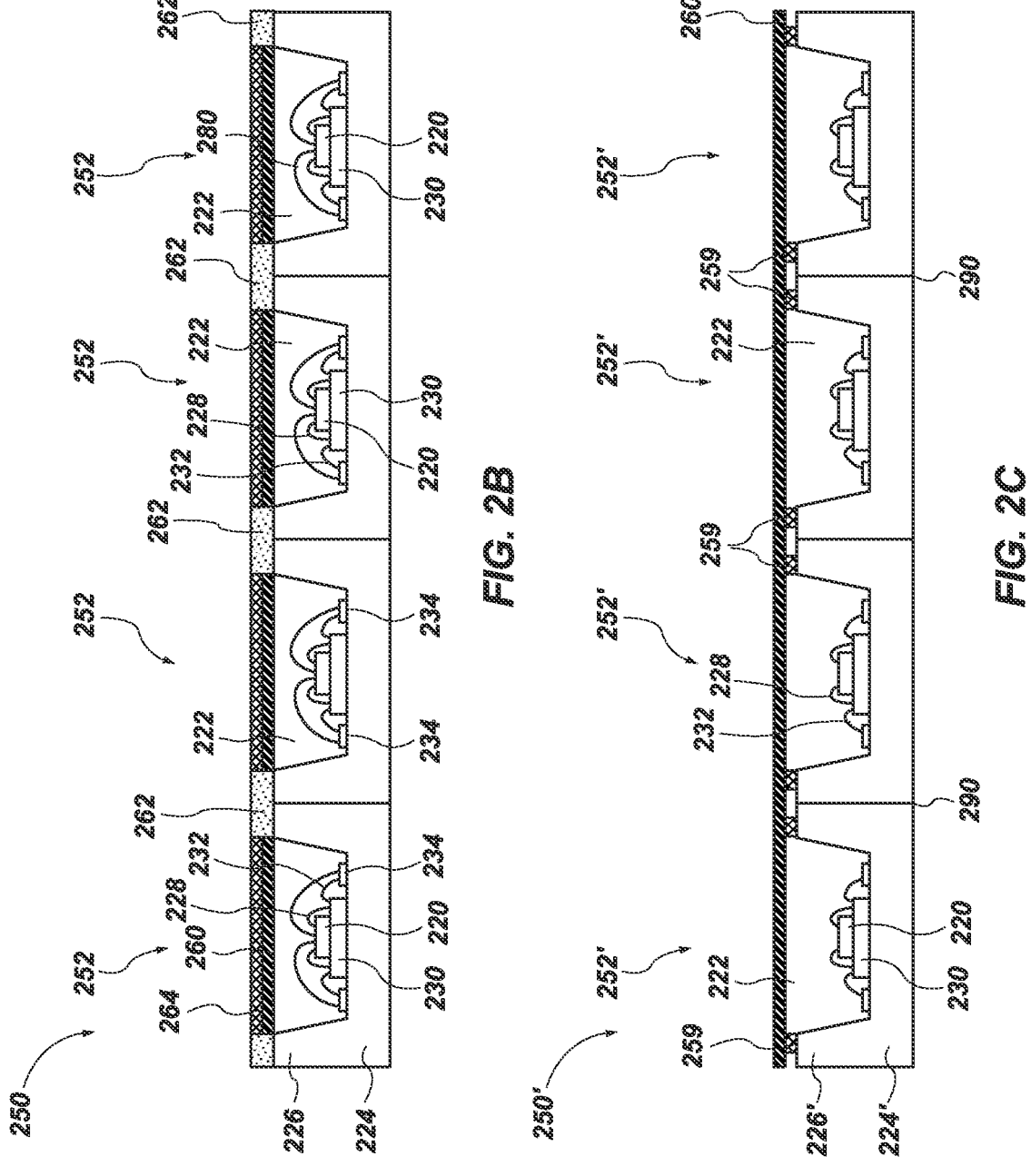
FIG. 2B through FIG. 2E illustrate fabrication acts of the method of FIG. 2A.

FIG. 2B is a simplified cross-sectional view of an array 250 of gas sensor device packages 252. The array 250 may be substantially the same as the array of FIG. 1B, except that the array 250 may not include the protective film 166. The array 250 may include a flame arrestor 260 bonded to the material of sidewalls 226 of a leadframe 224, such as to a thermoplastic material. A filter 264 may overlie the flame arrestor 260 and may be bonded to the sidewalls 226. In some embodiments, the filter 264 is bonded to the flame arrestor 260 at locations corresponding to a periphery of each of the gas sensor device packages 252. In some embodiments, the filter 264 is bonded to at least one of the flame arrestor 260 and the leadframe 224 with an adhesive, such as a b-staged adhesive.

Each gas sensor device package 252 may include at least one gas sensor die 220 in electrical communication with the package material 224, such as through an ASIC 230. In other embodiments, the gas sensor dice 220 may be directly coupled to the package material 224 and the gas sensor device package 252 may not include the ASIC 230. The at least one gas sensor die 220 may be wirebonded to the ASIC 230 with wirebonds 228 and the ASIC 230 may be wire-bonded to bond pads 234 of the leadframe 224 with wire-bonds 232, as described above with reference to FIG. 1B. In other embodiments, it will be understood that the gas sensor device packages 252 may include gas sensor dice 220 flip chip bonded to the leadframe 224, as described above with reference to FIG. 1D. In some embodiments, the at least one gas sensor die 220 may be wirebonded directly to the leadframe 224, such as with a wirebond 280 or may be flip chip mounted to the leadframe 224. In some such embodiments, the gas sensor device packages 252 may not include the ASIC 230.

The flame arrestor 260 and the filter 264 may be bonded to the sidewalls 226 of the package material 224 at bonding locations 262. At the bonding locations 262, the flame arrestor 260 and the filter 264 may be integral with the material of the sidewalls 226. In some embodiments, the material of the sidewalls 226 comprises a thermoplastic material (e.g., a liquid crystal polymer), which may substantially surround the material of the flame arrestor 260 and/or the material of the filter 264 at locations corresponding to the sidewalls 226.

In some embodiments, bonding at least one of the flame arrestor 260 and the filter 264 to the array 250 includes softening the material of the sidewalls 226 of each gas sensor device package 252 of the array 250 by heating the sidewalls 226 to at least a heat deflection temperature of the material of the sidewalls 226. When the sidewalls 226 are at the heat deflection temperature or at least to a Vicat softening temperature, the flame arrestor 260, the filter 264, or both may be swaged or pressed into the material of the sidewalls 226 to form, for example, the flame arrestor 260 and filter 264 disposed within the material of the sidewalls 226 at the sidewall locations.

In some embodiments, the filter 264 is bonded to the flame arrestor 260 at bonding locations 262 with an adhesive, such as a b-staged adhesive, a thermoplastic adhesive, epoxy, another suitable method for bonding the filter 264 to the flame arrestor 260, or combinations thereof. In some embodiments, the adhesive comprises polyurethane.

With reference to FIG. 2C, in other embodiments, bonding the at least one of the flame arrestor 260 and the at least one filter 264 over the method 200 of gas sensor device packages may include welding the flame arrestor 260 over an array 250' of gas sensor device packages 252'. Each gas sensor device package 252' may include a gas sensor die 220 attached to a leadframe 224', as described above with reference to FIG. 2B. In some embodiments, the gas sensor device packages 252' do not include the ASIC 230 and the gas sensor dice 220 are in direct electrical communication with the leadframe 224'.

The gas sensor dice 220 may be disposed in a cavity 222 defined by sidewalls 226' of the respective gas sensor device package 252' in which they are located. In some embodiments, the sidewalls 226' of the leadframe 224', the leadframe 224', or both may comprise a ceramic material (e.g., alumina), a metal can, or combinations thereof.

In some embodiments, a metal rings 259 is disposed over the array 250', such as around a periphery of each of the gas sensor device package 252' over the sidewalls 226' thereof at locations corresponding to saw streets 290 between the gas sensor device packages 252'. In some embodiments, the metal ring 259 may not be disposed over an entire saw street 290 of the array 250'. The metal ring 259 may be brazed to an upper surface of the array 250'. The metal ring 259 may comprise iron, nickel, cobalt, or combinations thereof. In some embodiments, the metal ring 259 comprises an alloy of iron, nickel, and cobalt.

In some embodiments, the flame arrestor 260 is welded to the upper surfaces of the metal ring 259. Accordingly, the flame arrestor 260 may extend over the array 250' of gas sensor device packages 252'.

In some embodiments, a filter may be disposed over the flame arrestor 260 and may extend over the array 250'.

The array 250' may be beneficial in embodiments including gas sensor dice formulated and configured for high sensitivity (e.g., parts per billion or less) detection of one or more analytes in a gas sample.

Act 206 includes sealing at least one of the flame arrestor or the at least one filter to the array of gas sensor device packages with a protective material or lid. In some embodiments, the protective material comprises the flame arrestor 260 and/or the filter 264. In other embodiments, the flame arrestor 260 and the filter 264 may be sealed to the array 250, 250' with a protective film (e.g., the protective film 166 (FIG. 1B)) to form an array as described above with reference to FIG. 1B. The protective film may comprise a thermoplastic material, nitrocellulose, a film, a tape, or a lid. In some embodiments, the protective film comprises a membrane. In some embodiments, the flame arrestor 260 and/or the filter 264 may be sealed with a protective film comprising an epoxy film, a polyimide material, a b-staged adhesive, a polyurethane adhesive, nitrocellulose, another material, or combinations thereof. In some embodiments, the protective film comprises a polyimide film. In other embodiments, the at least one of the flame arrestor 260 and the filter 264 is sealed with nitrocellulose configured to decompose responsive to exposure to ultraviolet light. In some embodiments, the protective film may be ink marked to provide tracability of one or more of the gas sensor device packages of the array. In some embodiments, the protective film comprises a thermoplastic material, such as a liquid crystal polymer.

In other embodiments, act 206 includes sealing the at least one of the flame arrestor 260 and the filter 264 with a lid extending over the gas sensor device package 252, as will be described with reference to FIG. 2E. Accordingly, act 206 may include sealing at least one of the flame arrestor 260 and the filter 264 with a planar protective film (e.g., the protective film 166 (FIG. 1B)), sealing the at least one of the flame arrestor 260 and the filter 264 in a lid, or both.

Act 208 includes singulating the array of gas sensor device packages to form a plurality of singulated gas sensor device packages. Singulating the array 250, 250' of gas sensor device packages 252 may include cutting the saw streets 290 (FIG. 2B, FIG. 2C) with a mechanical saw, with a laser, or a combination thereof, to separate individual gas sensor device packages 252, 252' from the array 250, 250'. Since each gas sensor device package 252, 252' includes the protective film over the flame arrestor 260, the gas sensor die 220 of each of the gas sensor device packages 252 may not be contaminated with the cuttings during singulation of the method 200.

Figure 2D:
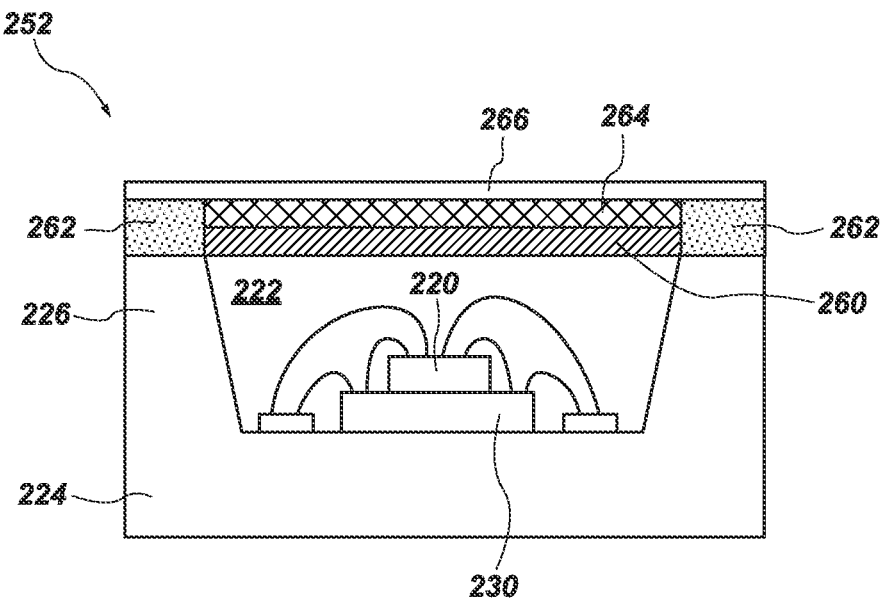

Each singulated gas sensor device package may include a gas sensor die 220 bonded to the leadframe 224, at least one of the flame arrestor 260 and the filter 264 bonded to the leadframe at least at sidewalls 226 thereof, and a protective film disposed over at least one of the flame arrestor 260 and the filter 264. FIG. 2D is a simplified cross-sectional view of a singulated gas sensor device package 252 in accordance with embodiments of the disclosure. The singulated gas sensor device package 252 includes at least one gas sensor die 220 disposed in the cavity 222 defined by the sidewalls 226 of the leadframe 224. The flame arrestor 260 and the filter 264 may be disposed over and cover the cavity 222. A protective film 266 (e.g., a thermoplastic material, a tape, a polyimide film) may be disposed over the flame arrestor 260 and the filter 264 extending over the cavity 222. The protective film 266 may extend over the bonding locations 262. Of course, where the array includes the metal rings 259, the gas sensor device package 252 may be similar to the gas sensor device packages 252' described above with reference to FIG. 2C and may include the protective film 266 thereover.

Figure 2E:
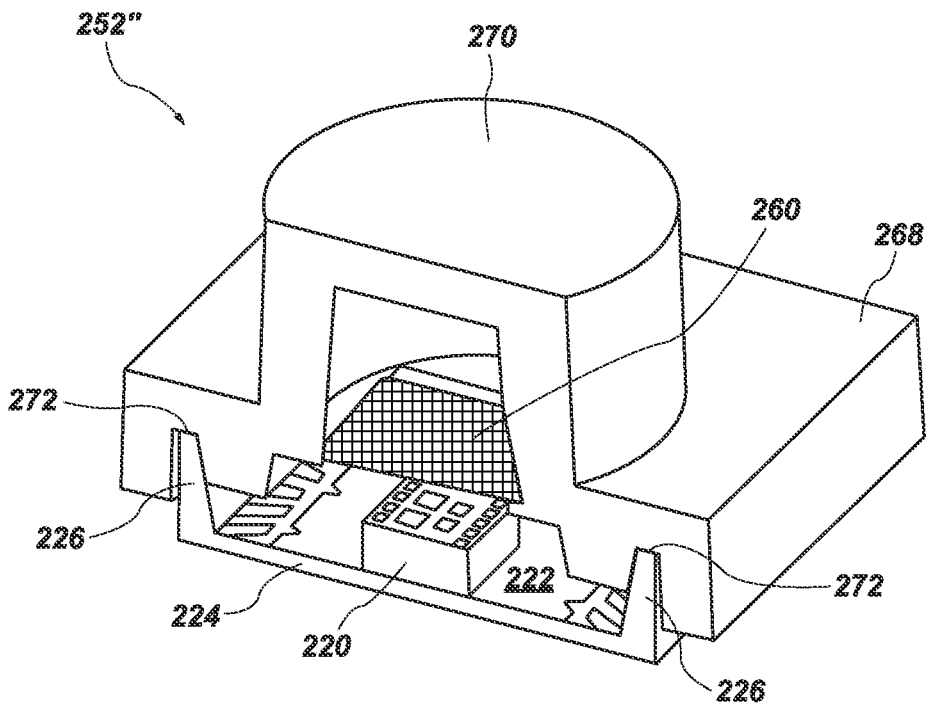

FIG. 2E is a simplified cutaway perspective view of a singulated gas sensor device package 252", in accordance with other embodiments of the disclosure. The gas sensor device package 252" may be substantially similar to the gas sensor device package 252 of FIG. 2D, except that the gas sensor device package 252" may include a protective lid (cap) 268 over the cavity 222, rather than the protective film 266. The gas sensor device package 252" includes the gas sensor die 220 disposed within the cavity 222 and electrically connected to the leadframe 224. The lid 268 includes a protuberance 270 extending in a direction away from a major surface of the leadframe 224. After singulation and assembly of the gas sensor device package 252' onto a final product assembly (e.g., a PCB), the protuberance 270 may extend far enough from the flame arrestor 260 that the protuberance 270 may be cut to expose the flame arrestor 260 and the gas sensor die 220 to the external environment.

The lid 268 may include recessed portions 272 defining a cavity configured to receive the sidewalls 226 of the leadframe 224. In some embodiments, the lid 268 comprises a thermoplastic material, such as a liquid crystal polymer material. The lid 268 may comprise the same material as the sidewalls 226. In some embodiments, the lid 268 is pressed into the leadframe 224 and the leadframe 224 and lid 268 are coupled via a compression fit. The leadframe 224 and the lid 268 may be coupled by heating the lid 268 and the sidewalls 226 to a thermal deflection temperature (e.g., a temperature between about 120° C. and about 300° C.) of the leadframe 224 and the lid 268 and pressing the sidewalls 226 into the recessed portions 272 of the lid 268. Alternatively, the lid 268 may be bonded to the leadframe 224 with an adhesive, such as a b-staged adhesive, a thermoplastic adhesive, epoxy, or combinations thereof. In some embodiments, the adhesive comprises polyurethane.

Act 210 includes assembling the singulated gas sensor device packages onto a printed circuit board or into sockets electrically coupled to a printed circuit board. In some embodiments, each gas sensor device package may be electrically coupled to a printed circuit board, such as by electrically coupling electrically conductive pads (e.g., the bond pads 134 (FIG. 1C)) of the leadframe 224 to conductive pins of the printed circuit board. By way of non-limiting example, the gas sensor device packages 252, 252', 252" may be surface mounted to a printed circuit board to form a printed circuit board assembly (PBCA) such as by electrically connecting conductive terminals (e.g., bond pads 134

(FIG. 1C)) of the leadframe 224 to conductive portions of the printed circuit board. In some embodiments, a flux, such as a water soluble flux paste may be used to surface mount the leadframe 224 of the gas sensor device package 252, 252', 252" to the printed circuit board. Forming the electrical connections may generate volatile organic compounds (VOCs) (such as those present in flux materials) used to form the electrical connections. However, the VOCs may contaminate the gas sensor dice. In addition, forming the electrical connections may generate dust, which may contaminate the gas sensor device and associated package. After surface mounting the gas sensor device package 252, 252', 252" to the printed circuit board, the printed circuit boards may be washed in hot water or solutions containing a saponifier to remove the water soluble flux paste. In some embodiments, the protective film 266 or the lid 268 may protect the gas sensor die 220 from being contaminated with water during water washing of the printed circuit board, and may further protect the gas sensor die 220 from dust or VOCs generated during surface mounting of the gas sensor device package 252 252', 252" to the printed circuit board.

Act 212 includes forming an opening (e.g., a vent) over a surface of the singulated gas sensor device packages. For example, an opening may be formed in the protective film 266 (FIG. 2D) to expose the flame arrestor 260 and place the gas sensor die 220 in fluid communication with an external environment. In some embodiments, the protective film 266 is peeled from over the top surface of the gas sensor device package 252 to expose the flame arrestor 260, the filter 264, and the gas sensor die 220 to the external environment. In other embodiments, the protective film 266 is removed by exposing the protective material to heat, ultraviolet light, or both. In some embodiments, the filter 264 may be removed from the array 100 with the protective film 266.

In embodiments where the gas sensor device package 252 comprises the lid 268 (FIG. 2E), an opening may be formed in the lid 268 or a portion of the protuberance 270 may be removed. In some embodiments, one or more openings are formed in the protuberance 270 by puncturing the protuberance 270 (e.g., passing a needle through the protuberance 270). In some embodiments, the needle may be heated to a temperature above a softening thermal deflection temperature of the material of the lid 268. In some embodiments, a length of the needle may be less than a distance between a surface of the protuberance 270 and the top surface of the flame arrestor 260. In other embodiments, a top portion of the protuberance is cut to form an opening in the gas sensor device package 252' and expose the gas sensor die 220 disposed therein. Accordingly, in some embodiments, the protective film 266 or the lid 268 protect the gas sensor die 220 during dicing of the array 250 of gas sensor device packages 252, and during attachment of the gas sensor device package 252 to a printed circuit board or within a socket. In some embodiments, the protective film 266 or the lid 268 are removed after attaching the gas sensor device package 252 to the printed circuit board or within a socket.

Although FIG. 2A has been described as bonding the filter 264 to the flame arrestor 260 or to the method 200 during act 204, the disclosure is not so limited. In other embodiments, the filter 264 is bonded directly to the sidewalls 226 and the method 200 does not include the flame arrestor 260.

FIG. 3A is a simplified flow diagram of a method 300 of forming an array of gas sensor device packages, in accordance with embodiments of the disclosure. The method 300 includes act 302 including attaching at least one gas sensor die of an array of gas sensor dice into at least one package of an array of packages to form an array of gas sensor device packages; act 304 including sealing the array with a protective material; act 306 including singulating the array of gas sensor device packages to form a plurality of singulated gas sensor device packages; act 308 including assembling the singulated gas sensor device packages onto a printed circuit board or into sockets electrically coupled to a printed circuit board to form an assembly; act 310 including removing the protective film from over the singulated gas sensor device packages; and act 312 including attaching at least one of a flame arrestor and a filter over the individual gas sensor device package assemblies.

Act 302 includes attaching at least one gas sensor die of an array of gas sensor dice into at least one package of an array of packages to form an array of gas sensor device packages. Act 302 may be substantially the same as act 202 described above with reference to FIG. 2A. Act 302 may include attaching gas sensor dice of an array of gas sensor dice into an array of packages (e.g., the package material 124 (FIG. 1C)) to electrically connect each gas sensor die to the package material and form an array of gas sensor device packages. As described above with reference to FIG. 2A, the gas sensor dice of the array may be bonded to the lead frame with conductive bumps and a fluxless flip chip method, by wirebonding conductive pads of each gas sensor die to the package material 124, or a combination thereof.

Figure 3B:
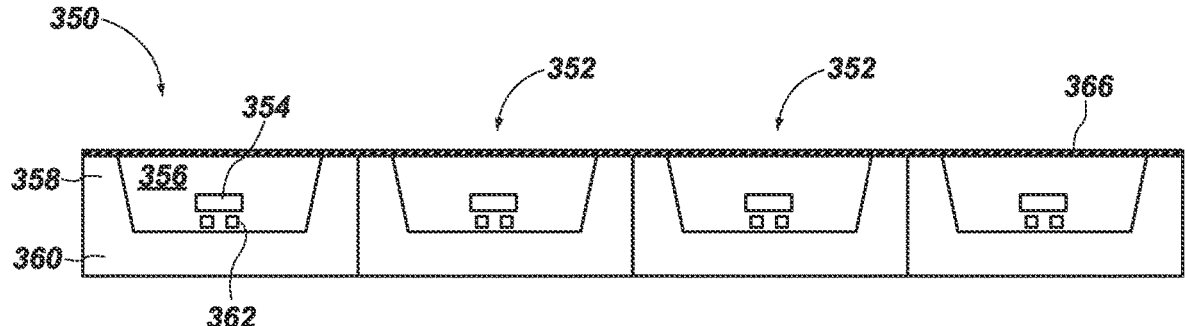
FIG. 3B through FIG. 3D illustrate fabrication acts of the method of FIG. 3A.

Act 304 includes sealing the array with a protective film. FIG. 3B is a simplified cross-sectional view of an array 350 including a plurality of gas sensor device packages 352, each gas sensor device package 352 including one or more gas sensor dice 354 disposed in a cavity 356 defined by sidewalls 358 of the gas sensor device package 352. The gas sensor device package 352 may be in electrical communication with a leadframe 360, such as with electrically conductive balls 362 (e.g., conductive bumps). In other embodiments, the gas sensor dice 354 may be in electrical communication with the leadframe 360 with bond wires electrically connecting bond pads of the gas sensor device package 352 to bond pads of the leadframe 360, through a redistribution layer, or a through silicon via, as described above with reference to FIG. 1B through FIG. 1G.

A protective film 366 may extend over the array 350 and overlie each of the gas sensor device packages 352. In some embodiments, the protective film 366 extends over the sidewalls 358 and covers the cavity 356 of each of the gas sensor device packages 352. The protective film 366 may include a film, a tape, or a lid. The protective film 366 may comprise, for example, polyimide, a protective tape, a self-developing resist (e.g., nitrocellulose), or another material.

Act 306 includes singulating the array of gas sensor device packages to form a plurality of singulated gas sensor device packages. Act 306 may be substantially similar to act 208 described above with reference to FIG. 2A. Since the array 350 includes the protective film 366 over each of the gas sensor device packages 352, the gas sensor device packages 352 may not be contaminated with cutting materials generated during singulation of the method 300 of gas sensor device packages 352. After singulation, each gas sensor device package 352 may include one or more gas sensor dice 354 electrically coupled to the package material 360 and the protective film 366 overlying and covering the cavity 356 of the gas sensor device package 352.

Figure 3C:
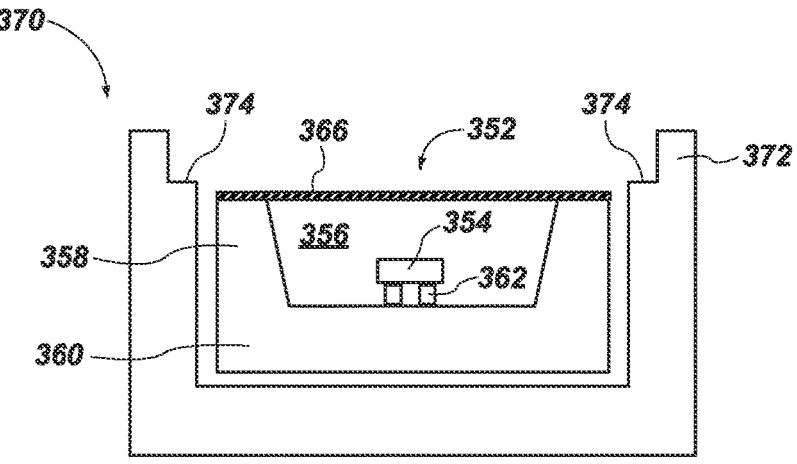

Act 308 includes assembling the singulated gas sensor device packages onto a printed circuit board or into sockets that are soldered to a printed circuit board. Act 308 may be substantially the same as act 210 described above with reference to FIG. 2A. FIG. 3C is a simplified cross-sectional view of an assembly 370 including a singulated gas sensor device package 352 disposed in a socket 372. The socket 372 may be electrically coupled to a printed circuit board or another component of a system. The assembly 370 may be in electrical communication with the socket 372, such as with through silicon vias, as described above. For example, electrically conductive portions of the package material 360 may be in electrical communication with the socket 372, which, in turn, may be in electrical communication with a printed circuit board.

The socket 372 may include surfaces 374 configured to receive a flame arrestor, a filter, or both, to cover the gas sensor device package 352 within the socket 372.

Since the singulated gas sensor device packages 352 include the protective film 366 thereover, the gas sensor dice 354 may not be contaminated with dust, water, or VOCs during surface mounting of the gas sensor device packages 352 to the socket 372 or mounting of the socket 372 to the printed circuit board.

Act 310 includes removing the protective material from over the singulated gas sensor device packages. The protective film 366 may be removed by, for example, peeling an adhesive material comprising the protective film 366 from over surfaces of the gas sensor device package 352, such as from over surfaces of the sidewalls 358 to expose the cavity 356. Accordingly, in some embodiments, the protective film 366 is removed after assembling the singulated gas sensor device packages onto a printed circuit board or into sockets that are soldered to a printed circuit board.

Figure 3D:
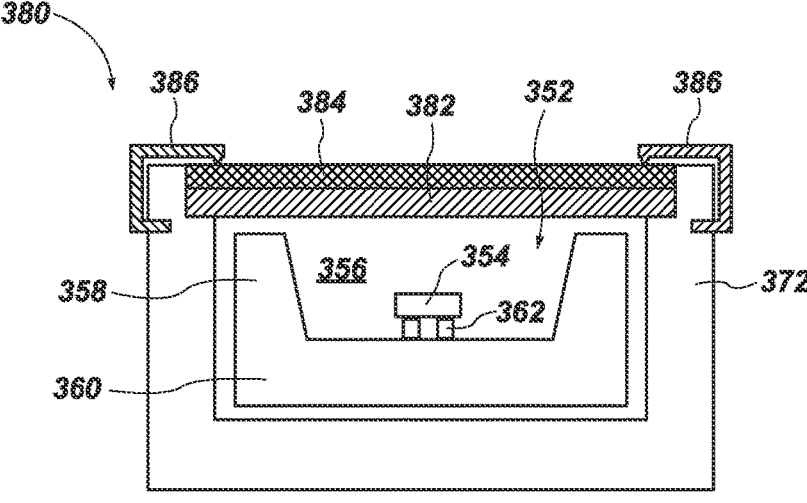

Act 312 includes attaching (e.g., bonding or clipping) at least one of a flame arrestor or a filter over the individual gas sensor device package assemblies or into a socket over the gas senor device package assembly. FIG. 3D is a simplified cross-sectional view of a system 380 including the gas sensor device package 352 disposed in the socket 372. A flame arrestor 382 may overlie the socket 372. The flame arrestor 382 may overlie the surfaces 374 (FIG. 3C) of the socket 372. In some embodiments, a filter 384 may overlie the flame arrestor 382.

The flame arrestor 382 and the filter 384 may be attached to the socket 372 with one or more retention means 386, such as clips. The retention means 386 may be biased toward the flame arrestor 382 and the filter 384 and may be configured to place a pressure on the sidewalls 358 to secure the flame arrestor 382 and the filter 384 in place over the socket 372. The retention means 386 may comprise a material formulated and configured to bias the flame arrestor 382 and the filter 384 toward the surfaces 374 of the socket 372. In other embodiments, the at least one of the flame arrestor 382 and the filter 384 may be bonded to the socket 372, such as with one or more adhesives.

Although FIG. 3D has been described and illustrated as including the retention means 386 over the socket 372, the disclosure is not so limited. In other embodiments, the flame arrestor 382, the filter 384, or both may be attached to a gas sensor device package 352 bonded to a printed circuit board or another component. In some such embodiments, the gas sensor device package 352 may include one or more surfaces configured to receive the retention means 386 for attaching the flame arrestor 382, the filter 384, or both directly to the gas sensor device package 352.

FIG. 4A is a simplified flow diagram of a method 400 of forming an array of gas sensor device packages, in accordance with embodiments of the disclosure. The method 400 includes act 402 including attaching at least one gas sensor die of an array of gas sensor dice into at least one package of an array of packages to form an array of gas sensor device packages; act 404 including assembling an integrated, bondable frame comprising at least one of a flame arrestor, a filter, or a protective material; act 406 including bonding the bondable frame to the array of gas sensor device packages; act 408 including singulating the array of gas sensor device packages to form a plurality of singulated gas sensor device packages; act 410 including assembling the singulated gas sensor device packages onto a printed circuit board or into sockets electrically coupled to a printed circuit board; and act 412 including removing the protective material from surfaces of the singulated gas sensor device packages.

Act 402 includes attaching gas sensor dice of an array of gas sensor dice into a package array to form an array of gas sensor device packages. Act 402 may be substantially the same as act 302 described above with reference to FIG. 3A. Act 402 may include attaching gas sensor dice of an array of gas sensor dice into a package array (e.g., the leadframe 124 (FIG. 1C)) to electrically connect each gas sensor die to the leadframe 124 and form an array of gas sensor device packages. As described above with reference to FIG. 2A, the gas sensor dice of the array may be bonded to the leadframe 124 with conductive bumps and a fluxless flip chip method, by wirebonding conductive pads of each gas sensor die to the leadframe 124, or a combination thereof.

Act 404 includes assembling an integrated, bondable frame comprising at least one of a flame arrestor, a filter, or a protective material (e.g., a moisture barrier) or lid. The protective film may be substantially the same as the protective film 366 described above. In some embodiments, the protective film comprises polyimide. In other embodiments, the protective film comprises nitrocellulose. Alternatively, a protective lid comprising an integral part of the bondable frame 450 may be used to seal the gas sensor device packages to be formed. The flame arrestor and the filter may be the same as described above with reference to FIG. 1B.

Figure 4B:
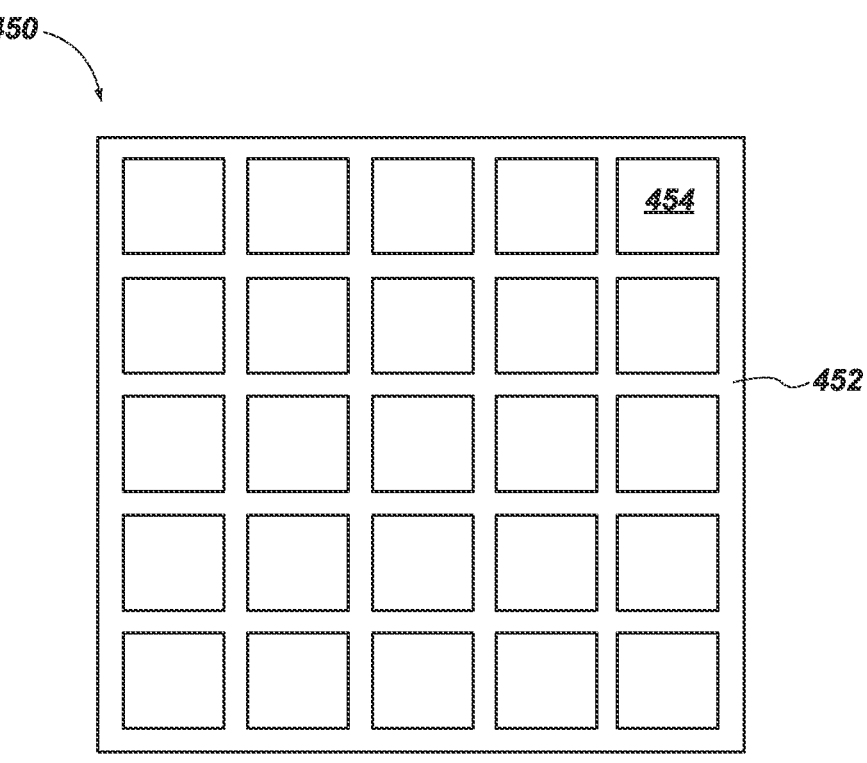
FIG. 4B through FIG. 4L illustrate fabrication acts of the method of FIG. 4A.

FIG. 4B is a simplified plan view of a bondable frame 450 prior to attachment to a flame arrestor, filter, or protective material. The bondable frame 450 includes saw streets 452 defining individual cells 454 sized and shaped to be disposed over individual gas sensor device packages, as will be described herein. The bondable frame 450 may include a material sized and shaped to be disposed over an array of gas sensor device packages to cover the array of gas sensor device packages with at least one of a flame arrestor, a filter, and a protective film. In some embodiments, the bondable frame 450 comprises a thermoplastic material or another pliable material.

Figure 4C:
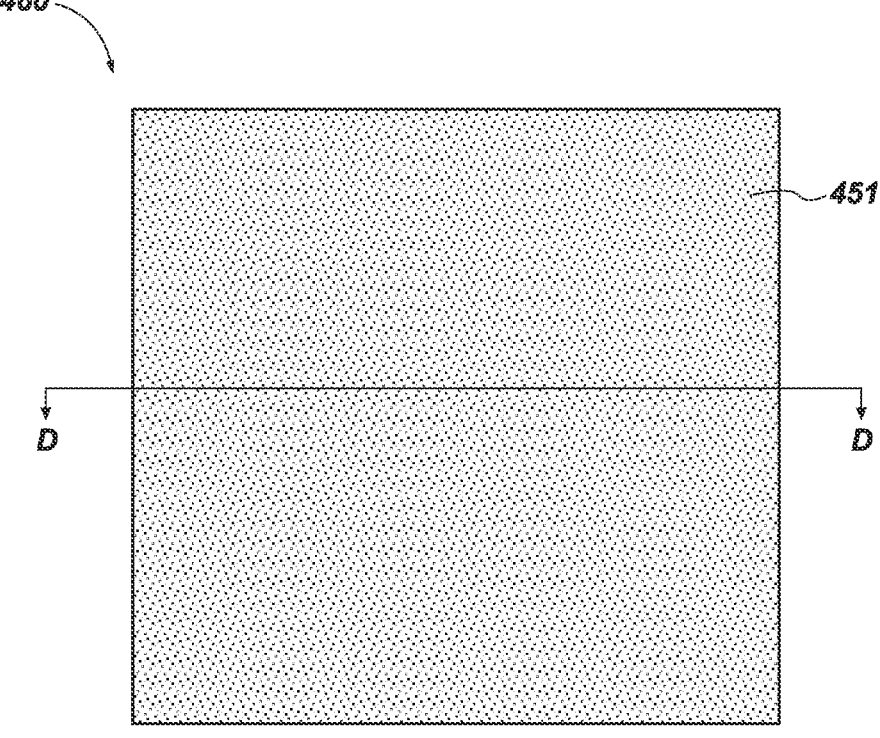

FIG. 4C is a simplified plan view of an assembly 460 including a material structure 451 comprising at least one of a flame arrestor, a filter, or a protective material. In some embodiments, the material structure 451 includes only the flame arrestor. In other embodiments, the material structure 451 includes the flame arrestor and a filter overlying and bonded to the flame arrestor. In further embodiments, the material structure 451 includes the flame arrestor, at least one filter overlying and bonded to the flame arrestor, and a protective film over the at least one gas filter. In yet other embodiments, the material structure 451 only the filter or the protective film overlying the filter and does not include a flame arrestor.

Figures 4D, 4E:
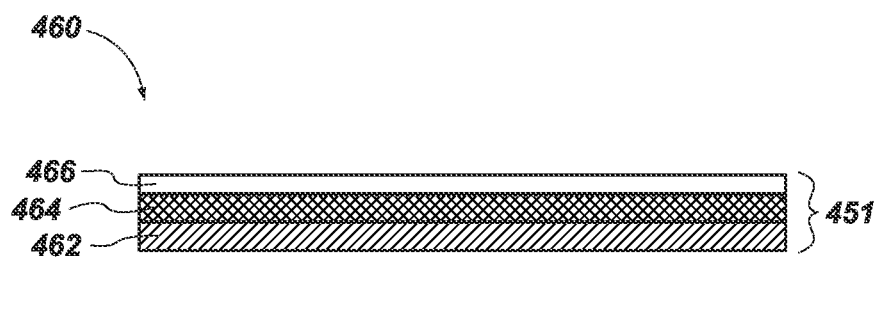

FIG. 4D is a simplified cross-sectional view of the assembly 460 taken along section line D-D of FIG. 4C. The material structure 451 may include a flame arrestor 462, a filter 464 over the flame arrestor 462, and a protective film 466 (e.g., the protective material) over the filter 464. However, the disclosure is not so limited and the assembly may not include one or more of the flame arrestor 462, the filter

464, and the protective film 466. In addition, in some embodiments, the flame arrestor 462 may be over the filter 464. FIG. 4E is a simplified plan view of a bonded frame 453 including the assembly 460 (FIG. 4C) bonded to the bondable frame 450 (FIG. 4B). In some embodiments, the bondable frame 450 may be heated to above a heat deflection temperature thereof and the assembly 460 may be pressed into the bondable frame 450 to form the bonded frame 453. In some embodiments, the assembly 460 is bonded to the bondable frame 450, such as by thermal compression, an adhesive, another method, or combinations thereof. In some embodiments, after the assembly 460 (FIG. 4C) is bonded to the bondable frame 450 (FIG. 4B), at least a portion of one or more of the flame arrestor 462, the filter 464, and the protective film 466 may be located within the cells 454 (FIG. 4B). Although FIG. 4E illustrates the saw streets 452, it will be understood that the saw streets 452 may be covered by the overlying assembly 460.

Figure 4F:
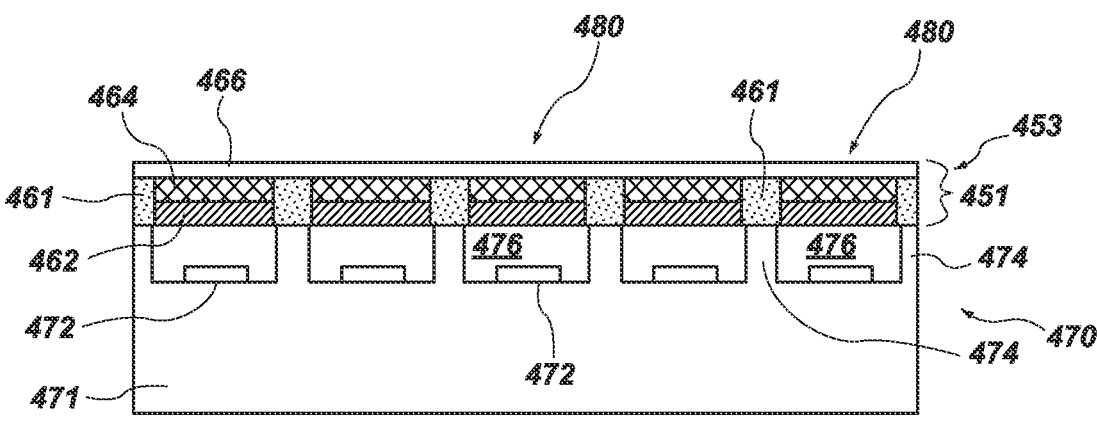

Act 406 includes bonding the bonded frame 453 to the array of gas sensor device packages. FIG. 4F is a simplified cross-sectional view of the bonded frame 453 attached to an array 470 of gas sensor device packages 480. The bonded frame 453 may be attached to the array of gas sensor device packages 480 at bonding locations 461, which may be substantially the same as the bonding locations 162 described above. In some embodiments, the bonding locations 461 may include locations where the material of the sidewalls 474 is integral with one or more of the flame arrestor 462 and the filter 464. In other embodiments, the bonding locations 461 may comprise an adhesive.

The gas sensor device packages 480 may be substantially the same as the gas sensor device packages 110, 110', 110", 252, 352 described above. For example, the array 470 may include a plurality of gas sensor device packages 480, each gas sensor device package 480 including at least one sensor die 472 bonded to a leadframe 471. Each gas sensor device package 480 may be defined by sidewalls 474 extending from a base of the leadframe 471 and defining a cavity 476. Although FIG. 4F illustrates that the sidewalls 474 extend substantially perpendicularly from the base of the package material 471, the disclosure is not so limited and the sidewalls 474 may be angled, as described above with reference to FIG. 1B.

The bonded frame 453 may contact the array 470 at upper surfaces of at least the sidewalls 474 at the bonding locations 461, at least a portion of which sidewalls 474 may define the saw streets 452 (FIG. 4E). After contacting the array 470 with the bonded frame 453, the bonded frame 453 may be bonded to the array 470. In some embodiments, the bonded frame 453 is bonded to the array 470 by applying pressure and heat to the bonded frame 453 and the array 470. In some embodiments, the bonded frame 453 and the array 470 are heated to above a heat deflection temperature of a thermoplastic material from which the sidewalls 474 are formed and the bonded frame 453 is pressed into the sidewalls 474 of the array 470 at the bonding locations 461. In an alternative embodiment, the bonded frame 453 may be attached to the array 470 at sidewalls with an adhesive, such as a b-staged adhesive, a thermoplastic adhesive, epoxy, or combinations thereof. In some embodiments, the adhesive comprises polyurethane.

Figure 4G:
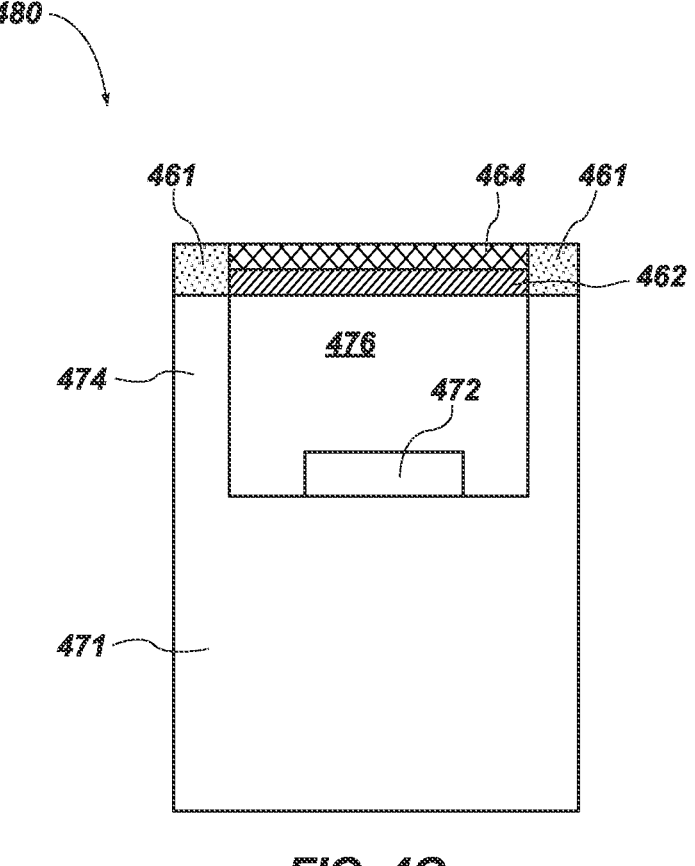

Act 408 includes singulating the array of gas sensor device packages to form a plurality of singulated gas sensor device packages. Act 408 may be substantially the same as act 210 described above with reference to FIG. 2A. Since the array 470 includes at least one protective material (e.g., protective film 466, the flame arrestor 462, the filter 464) on the bonded frame 453, the gas sensor device packages 480 may not be contaminated with cutting materials generated during singulation of the array of gas sensor device packages 480. With reference to FIG. 4G, after singulation, each gas sensor device package 480 may include an integrated assembly comprising the flame arrestor 462 over the gas sensor device package 480, a gas filter 464 over the flame arrestor 462, and the protective film 466 over the gas filter. The flame arrestor 462 and the filter 464 may be sealed to the gas sensor device package 480, such as at the sidewalls 474.

Act 410 includes assembling the singulated gas sensor device packages onto a printed circuit board or into sockets electrically coupled to a printed circuit board. Act 410 may be substantially the same as act 210 or act 312 described above with reference to FIG. 2A and FIG. 3A, respectively. In some such embodiments, each gas sensor device package 480 may be electrically coupled to a printed circuit board, such as by electrically coupling electrically conductive pads of the leadframe 471 (e.g., the bond pads 134 (FIG. 1C)) to conductive pins of the printed circuit board. Since the singulated gas sensor device package 480 includes the protective film 466 over the flame arrestor 462 and the filter 464, water or other contaminants may not enter the cavity 476 and contaminate or damage the gas sensor dice 472 during surface mounting of the gas sensor device packages 480 onto a printed circuit board or during water washing the flux used during surface mounting. In addition, the protective film 466 may protect the gas sensor die 472 from contamination from dust and/or VOCs generated during surface mounting of the gas sensor device package 480 to the printed circuit board. Accordingly, in some embodiments, the protective film 466 is removed after assembling the singulated gas sensor device packages onto a printed circuit board or into sockets that are soldered to a printed circuit board.

Act 412 includes removing the protective film 466 from over surfaces of the singulated gas sensor device packages. The protective film 466 may be removed by, for example, peeling the adhesive material of the protective film 466 from over surfaces of the filter 464, the flame arrestor 462, or the bondable frame 450, depending on the particular configuration of the singulated gas sensor device package 480.

Figure 4H:
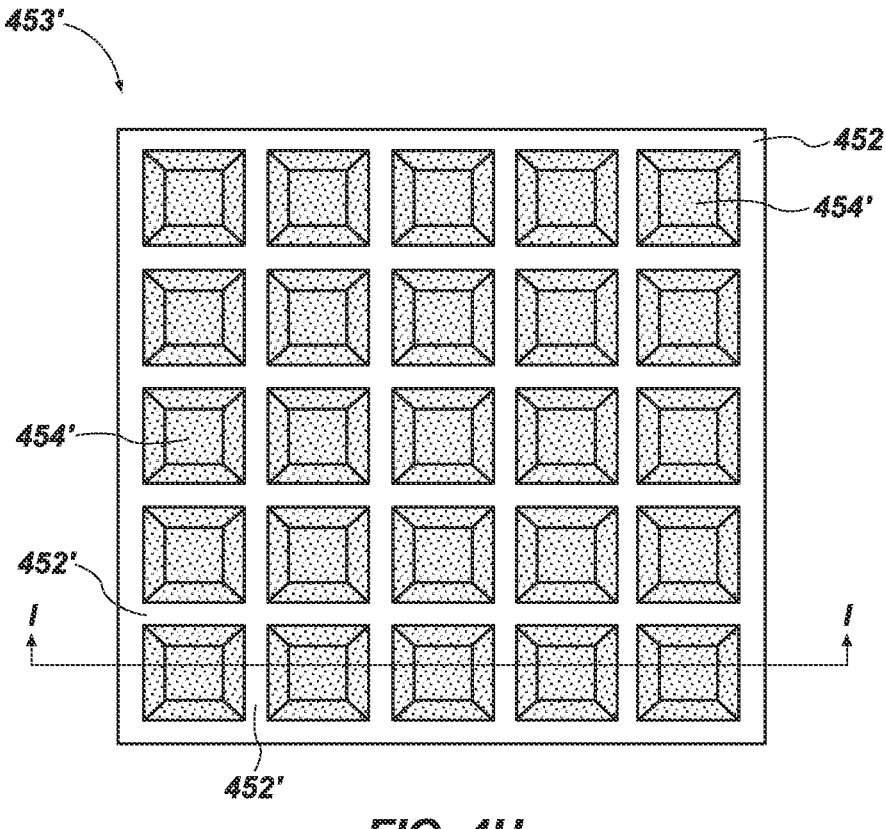

Although FIG. 4D through FIG. 4F illustrate that the protective film 466 comprises a substantially planar material, the disclosure is not so limited. With reference to FIG. 4H, in other embodiments, a bonded frame 453' may include a plurality of cells 454' (which may correspond to a location of individual gas sensor device packages of an array of gas sensor device packages) defined between saw streets 452' of the bonded frame 453'. The bonded frame 453' may include a bondable frame, which may be substantially the same as the bondable frame 450 described with reference to FIG. 4B.

Figure 4I:
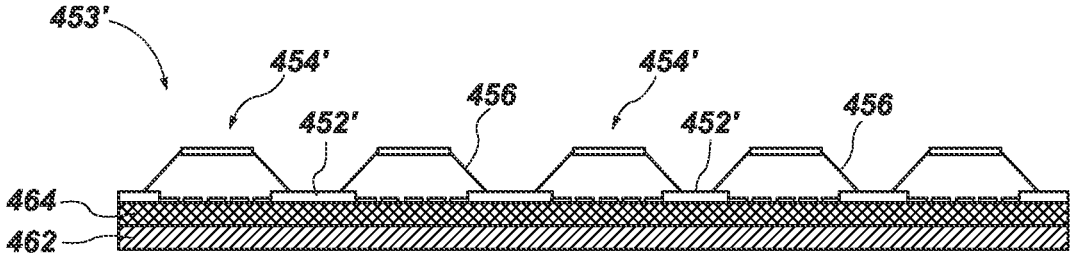

FIG. 4I is a cross-sectional view of the bonded frame 453' taken along section line I-I of FIG. 4H. The bonded frame 453' may include at least one of a flame arrestor 462 and a filter 464. A cap 456 may extend over each of the cells 454'. In some embodiments, the cap 456 comprises a thermoplastic material, such as a liquid crystal polymer material and may be adhered to the filter 464 (or the flame arrestor 462) with an adhesive, for example. The cap 456 may comprise a protuberance extending over a flame arrestor enclosed by the cap 456. The cap 456 may extend over the cells 454' at portions corresponding to locations of the saw streets 452' and may be separated from one another by the saw streets 452'.

Figure 4J:
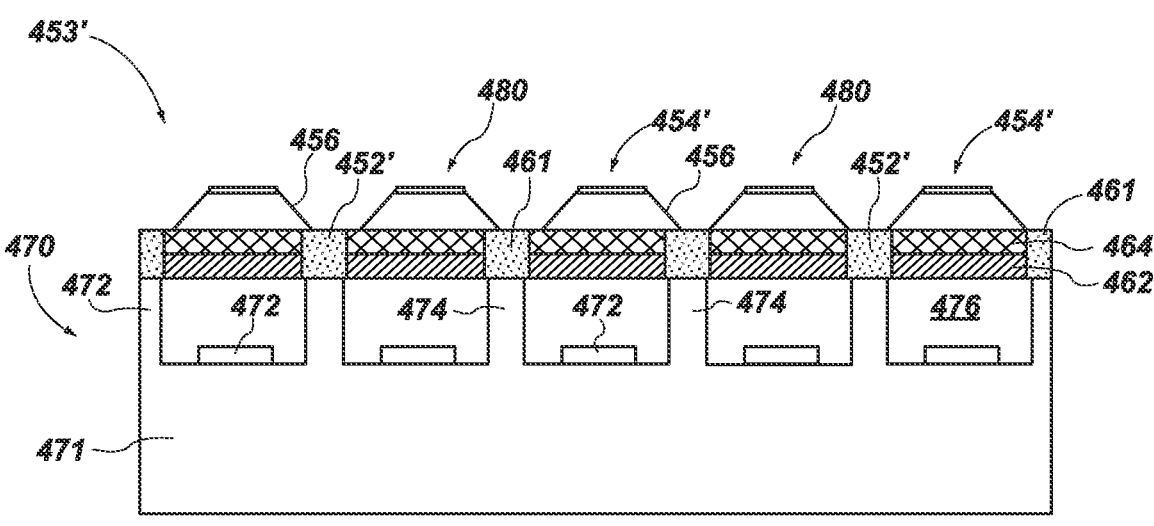

In embodiments including the bonded frame 453', act 406 may include bonding the bonded frame 453' to an array 470, as described above with reference to FIG. 4F. FIG. 4J is a simplified cross-sectional view of the bonded frame 453' after attachment thereof to the array 470. The array 470 may be the same as described above with reference to FIG. 4F. The bonded frame 453' may be attached to the array 470 at bonding locations 461, as described above with reference to the bonded frame 453 and the array 470.

Figure 4K:
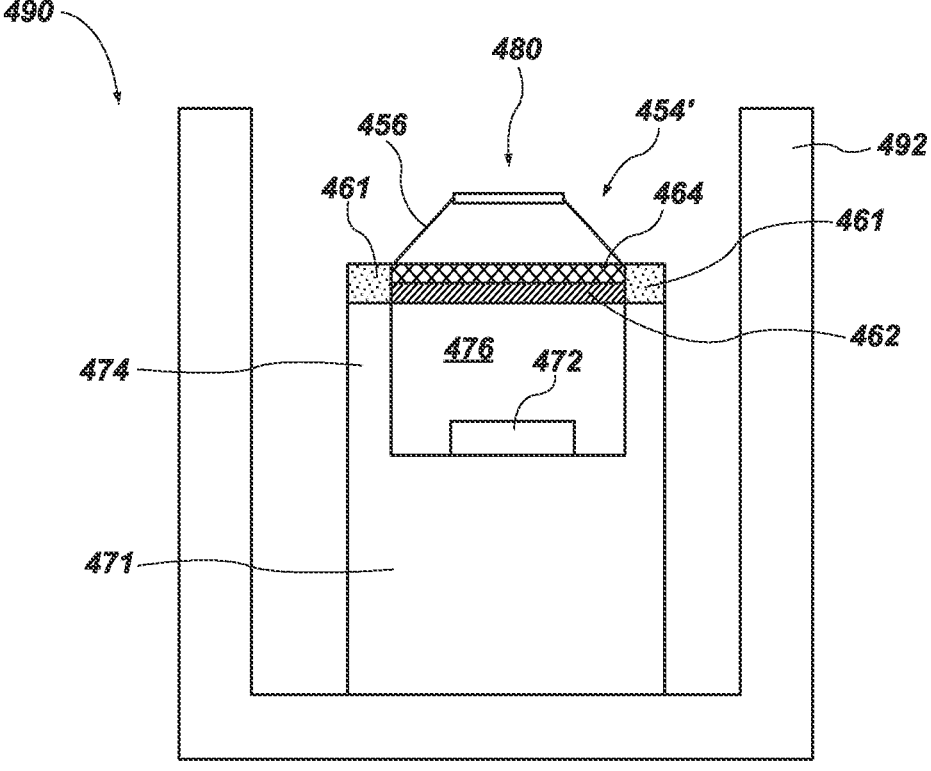

Singulation of the array 470 may form singulated gas sensor device packages 480, as shown in FIG. 4K. Since the array 470 includes the cap 456 over each gas sensor device package 480, the gas sensor device packages 480 may not be contaminated with cutting materials generated during singulation of the array 470 of packages. After singulation, each gas sensor device package 480 may include one or more gas sensor dice 472 electrically coupled to the leadframe 471 and the cap 456 overlying and covering the cavity 476 of the gas sensor device package 480.

In some embodiments, act 410 includes disposing the gas sensor device package 480 into sockets electrically coupled to a printed circuit board. With reference to FIG. 4K, the gas sensor device package 480 may be disposed and electrically coupled to a socket 492 to form an assembly 490. The gas sensor device package 480 may be in electrical communication with the socket 492 with, for example, one or more through silicon vias. In other embodiments, the gas sensor device package 480 may be wirebonded to the socket 492. In some embodiments, the socket 492 includes terminals configured to electrically couple to bond pads or lead fingers of the gas sensor device package 480.

Figure 4L:
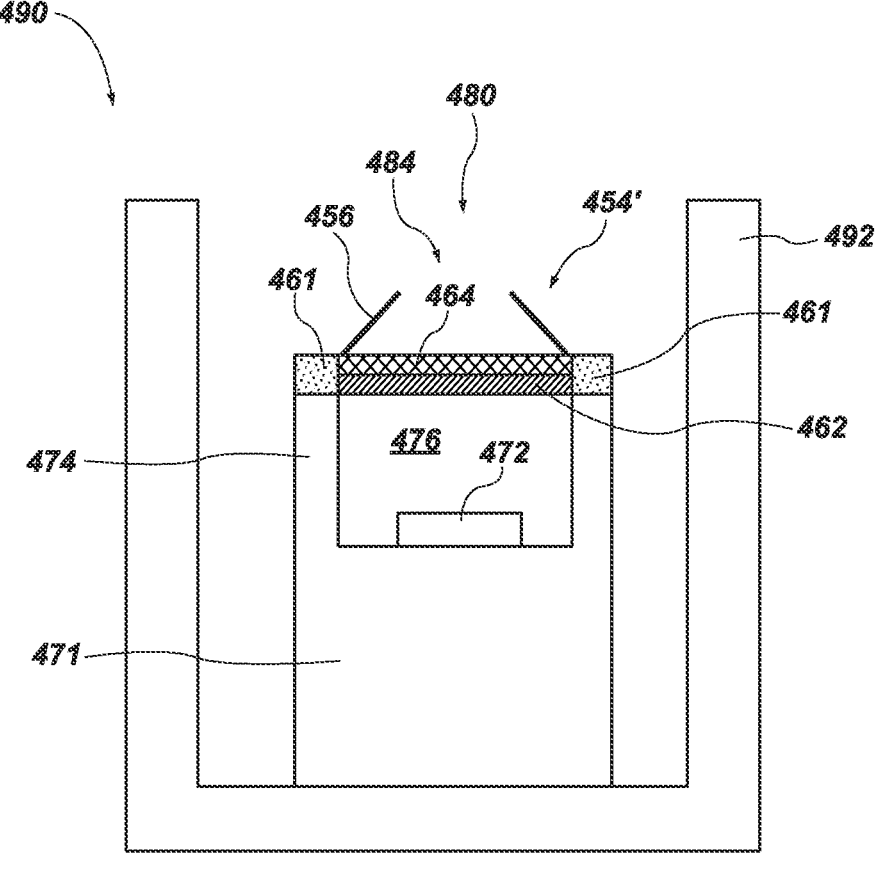

With reference to FIG. 4L, act 412 may include forming an opening 484 in the cap 456 (FIG. 4K). In some embodiments, act 412 is performed after surface mounting the gas sensor device packages 480 into the sockets 492 and water washing the resulting assemblies 490.

Forming the opening 484 in the cap 456 may expose the gas sensor die 472 to an ambient environment (e.g., to gas samples to be tested and analyzed). In some embodiments, the opening 484 is formed by cutting the cap 456. In other embodiments, one or more openings 484 are formed by forming one or more holes (e.g., puncturing) through the cap 456, such as with a needle.

Figure 5A:
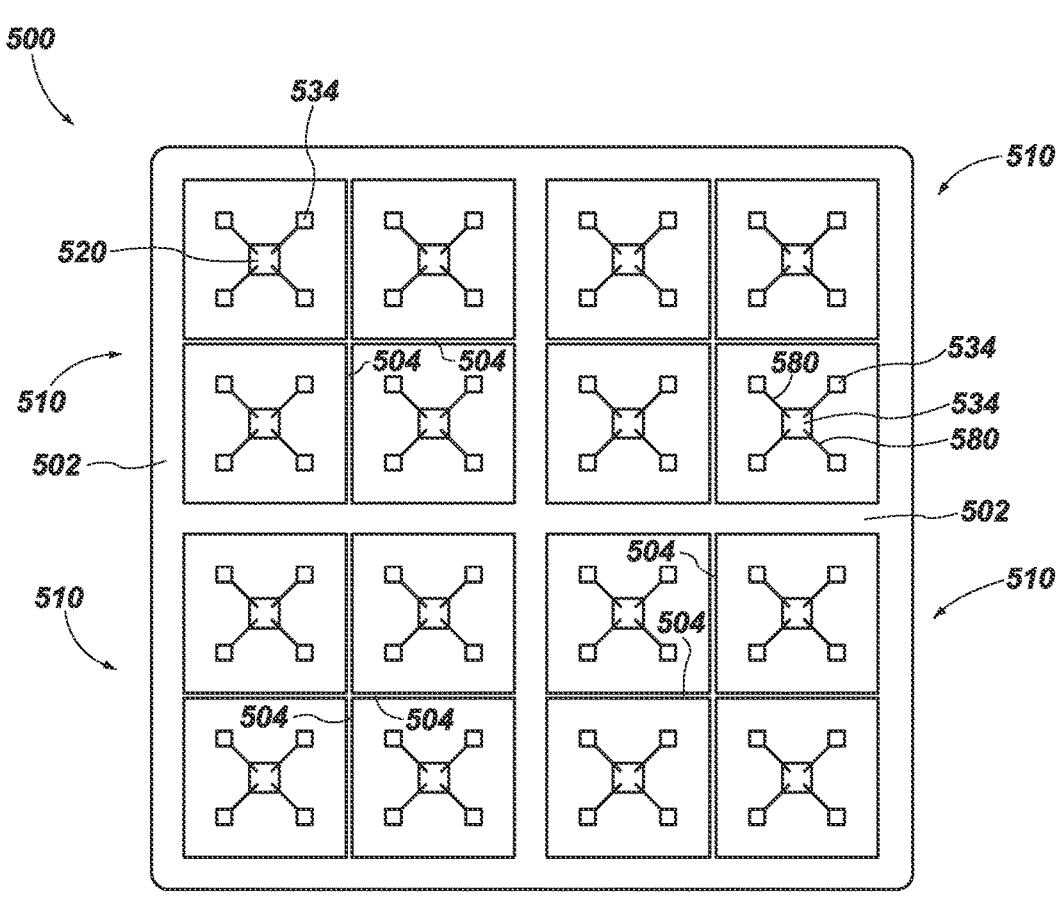
FIG. 5A and FIG. 5B are a respective top view and a simplified exploded cross-sectional view of an array of gas sensor device packages, in accordance with embodiments of the disclosure.
Figure 5B:
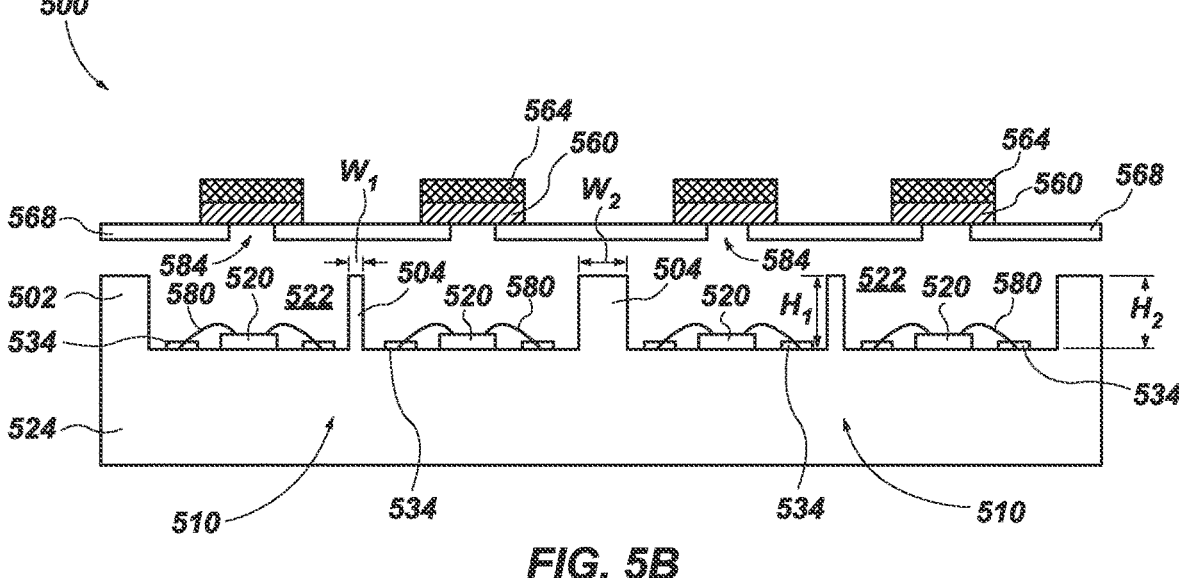

In yet other embodiments, an array of gas sensor device packages may include at least one gas sensor device package including a plurality of gas sensor dice separated from one another. FIG. 5A is a simplified plan view of a gas sensor device package array 500. FIG. 5B is a simplified cross-sectional exploded view of the gas sensor device package array 500 including a lid 568 thereover. With reference to FIG. 5A and FIG. 5B, the gas sensor device package array 500 may include a plurality of gas sensor device packages 510, wherein each gas sensor device package 510 includes a plurality of dice 520, which may comprise, for example, one or more gas sensor dice and/or one or more non-sensor dice (e.g., other electronic device, such as, for example, an ASIC, a processor, etc.). In some embodiments, at least some of the gas sensor device packages 510 include gas sensor dice and non-sensor dice, which may be separated from each other by walls 504. The gas sensor device packages 510 may be formed in a leadframe 524. The leadframe 524 may be substantially the same as the leadframe 124 described above with reference to FIG. 1B and FIG. 1C. By way of non-limiting example, the leadframe 524 may comprise a thermoplastic material, a ceramic material, or a metal material. In some embodiments, the leadframe 524 comprises bond pads 534 configured to be placed in electrical communication with components of the dice 520, such as through bond wires 580.

The gas sensor device packages 510 may be separated from each other by saw streets 502. Although FIG. 5A illustrates four gas sensor device packages 510, the disclosure is not so limited and the gas sensor device package array 500 may include more than four gas sensor device packages 510, such as more than about 1,000, more than about 10,000, or more than about 100,000 gas sensor device packages 510. Similarly, although FIG. 5A illustrates that each gas sensor device package 510 includes four dice 520, the disclosure is not so limited. In other embodiments, the gas sensor device packages 510 may include more dice 520, such as more than four dice 520, such as more than about 1,000, more than about 10,000, or more than about 100,000 dice 520. In some embodiments, different gas sensor device packages 510 may include a different number of dice 520 than other gas sensor device packages 510 in the gas sensor device package array 500.

The dice 520 of each gas sensor device package 510 may be separated from each other by walls 504. The walls 504 may comprise the same material as the saw streets 502. In some embodiments, the walls 504 have a width $W_1$ less than a width $W_2$ of the saw streets 502. In some embodiments, a height $H_1$ of the walls 504 may be about the same as a height $H_2$ of the saw streets 502.

The walls 504 may define a cavity 522 separating dice 520 of one gas sensor device package 510 from other dice 520 of the same gas sensor device package 510. In some embodiments, each gas sensor device package 510 may include different dice 520 (e.g., a MOS sensor, a resonant sensor, a thermal conductivity sensor, a catalytic microhotplate sensor, an environmental sensor (e.g., a sensor configured to determine one or more of a temperature, a pressure, and a humidity)), a processor, an ASIC, another electronic device, or combinations thereof.

The lid 568 may be configured to substantially cover the gas sensor device packages 510. The lid 568 may be bonded to the leadframe 524, such as at the saw streets 502 and the walls 504. In some embodiments, the leadframe 524 comprises a thermoplastic material (such as at the saw streets 502 and the walls 504), is heated to a temperature of about a thermal deflection temperature or above a softening thermal deflection temperature thereof, and the lid 568 is pressed into the saw streets 502 and the walls 504 to bond the lid 568 to the leadframe 524.

The lid 568 may include openings 584 (also referred to as vents) for providing fluid communication between the cavities 522 and an external environment (e.g., to expose the dice 520 to one or more gas samples during use and operation of the gas sensor device package 510). In some embodiments, cavities 522 not including dice 520 comprising gas sensors and including dice 520 comprising other electronic devices (e.g., ASIC dice, processors, etc.) may not include the openings 584.

At least one of a flame arrestor 560 or a filter 564 may overlie the lid 568. The flame arrestor 560 and the filter 564 may be substantially the same as the flame arrestor 160 and the filter 164, respectively, described above with reference to FIG. 1B. In some embodiments, the gas sensor device package array 500 includes only the filter 564 or only the flame arrestor 560 over the lid 568.

The at least one of the flame arrestor 560 and the filter 564 may be formed over the gas sensor device package array 500 after the openings 584 are formed in the lid 568.

In some embodiments, the at least one of the flame arrestor 560 and the filter 564 over a cavity 522 including a gas sensor die 520 may be different than the at least one of the flame arrestor 560 and the filter 564 over another cavity

522 including another gas sensor die 520 of the same gas sensor device package 510. In other embodiments, at least some cavities 522 of a gas sensor device package 510 may be covered with a flame arrestor 560 and optionally a filter 564, and at least other cavities 522 of the gas sensor device package 510 may be covered with only a filter 564.

Figure 5C:
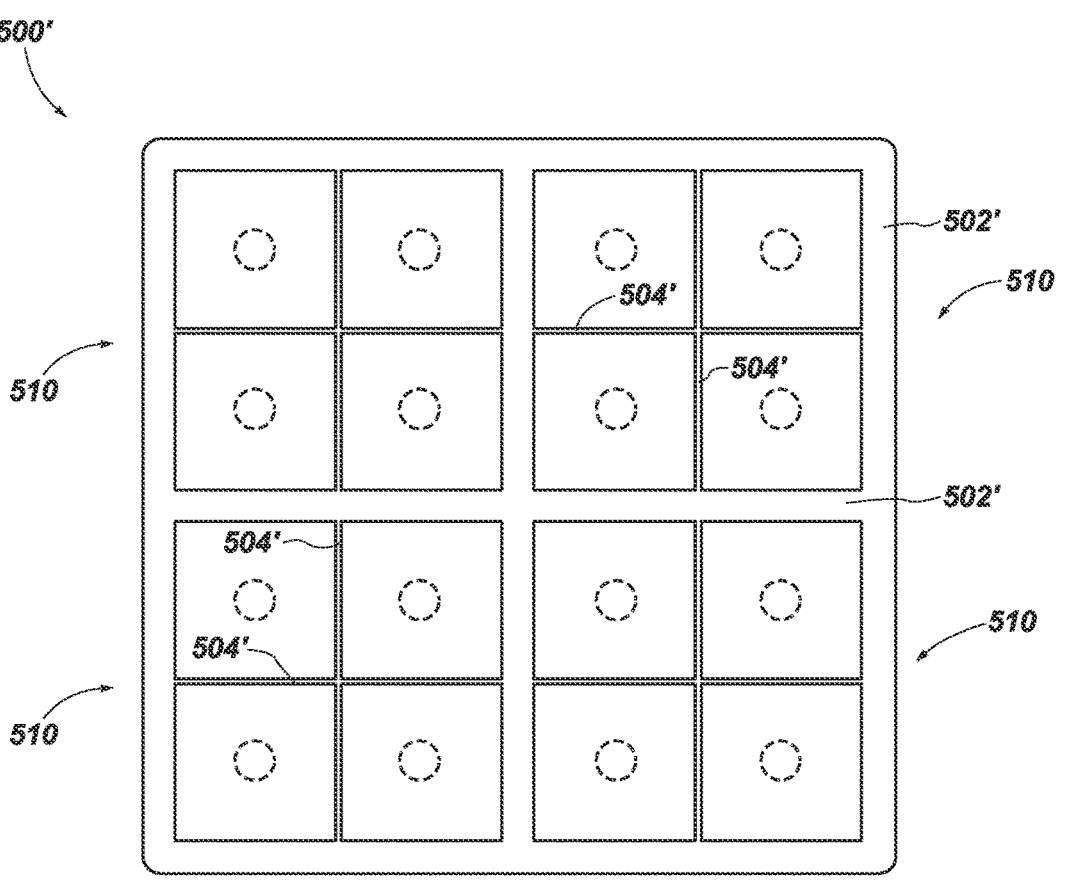
FIG. 5C and FIG. 5D are respective top view and a simplified exploded cross-sectional view of an array of gas sensor device packages, in accordance with other embodiments of the disclosure.
Figure 5D:
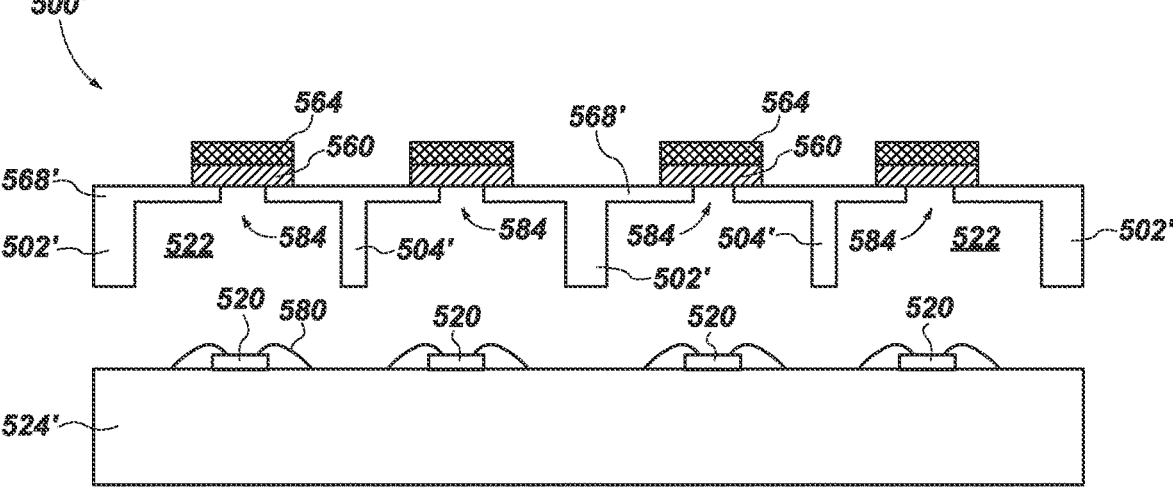

FIG. 5C is a simplified plan view of a gas sensor device package array 500' and FIG. 5D is a simplified cross-sectional exploded view of the gas sensor device package array 500', in accordance with other embodiments of the disclosure. With reference to FIG. 5C and FIG. 5D, the gas sensor device package array 500' may be substantially similar to the gas sensor device package array 500 of FIG. 5A and FIG. 5B, except that the gas sensor device package array 500' may include walls 504' and saw streets 502' located on a lid 568' rather than on a leadframe 524'. Accordingly, the leadframe 524' may include a substantially flat surface on which the gas sensor dice 520 are disposed and bonded to the bond pads 534.

The lid 568' includes saw streets 502', which may be located to separate individual gas sensor device packages 510 from other gas sensor device packages 510. The lid 568' may further include the walls 504', which may be located to separate individual gas sensor dice 520 within a gas sensor device package 510 from other gas sensor dice 520 within the gas sensor device package 510.

The lid 568' may be bonded to the leadframe 524' at locations corresponding to the saw streets 502' and the walls 504'.

Openings 584 in the lid 568' may be covered with at least one of the flame arrestor 560 or the filter 564, as described above with reference to FIG. 5A and FIG. 5B. The gas sensor device packages 510 may be singulated by cutting the gas sensor device package array 500' at the saw streets 502'.

Accordingly, an array of gas sensor device packages may be fabricated substantially simultaneously. The gas sensor device packages of the array may include at least one of an integral flame arrestor disposed over and bonded to the array, one or more filters, a protective film, and/or a lid disposed over the gas sensor device packages of the array. The array, which may include the integral flame arrestor, the one or more filters, the protective film, and/or the lid may be singulated. Since the gas sensor device packages include the protective material or the lid during dicing thereof, the gas sensor dice of the gas sensor device packages may be protected from dust, water, VOCs, and other contaminants that may damage the sensitivity and effectiveness of the gas sensor dice for sensing at least one property of at least one analyte of interest in a gas sample. In some embodiments, after a socket or the gas sensor device package is mounted (e.g., surface mounted) to a printed circuit board to form a system, the system is washed, such as in hot water to remove flux materials. After washing and drying the protective material or the lid may be removed or one or more openings may be formed therein to expose the gas sensor dice to an external environment. Each singulated gas sensor device may include an integrated flame arrestor and optionally, an integrated gas filter.

Additional non-limiting example embodiments of the disclosure are described below.

Embodiment 1: An array of gas sensor device packages, the array comprising: a plurality of gas sensor device packages, each gas sensor device package comprising a lead frame including bond pads and at least one gas sensor die in electrical communication with the bond pads, the gas sensor device packages each comprising at least one vent; and a protective covering over the plurality of gas sensor device packages.

Embodiment 2: The array of gas sensor device packages of Embodiment 1, further comprising a flame arrestor coupled to at least one of the protective covering or sidewalls of at least one gas sensor device package of the plurality of gas sensor device packages.

Embodiment 3: The array of gas sensor device packages of Embodiment 2, wherein the flame arrestor comprises a unitary material disposed over the plurality of gas sensor device packages.

Embodiment 4: The array of gas sensor device packages of Embodiment 2 or Embodiment 3, wherein the flame arrestor is coupled to the at least one of the protective covering or sidewalls of at least one gas sensor device package of the plurality of gas sensor device packages with glue, epoxy, or is integral with a thermoplastic material defining the sidewalls.

Embodiment 5: The array of gas sensor device packages of any one of Embodiments 1 through 4, wherein the protective covering comprises a temporary protective covering over the vent of at least one gas sensor device package.

Embodiment 6: The array of gas sensor device packages of any one of Embodiments 1 through 5, wherein the protective covering comprises a continuous material over the array of gas sensor device packages.

Embodiment 7: The array of gas sensor device packages of any one of Embodiments 1 through 6, further comprising saw streets defining individual gas sensor device packages of the array of gas sensor device packages.

Embodiment 8: The array of gas sensor device packages of any one of Embodiments 1 through 7, wherein the protective covering covers one or more vents in the plurality of gas sensor device packages.

Embodiment 9: The array of gas sensor device packages of any one of Embodiments 1 through 8, wherein the protective covering comprises nitrocellulose.

Embodiment 10: The array of gas sensor device packages of any one of Embodiments 1 through 9, wherein the protective covering comprises a protuberance extending in a direction away from the lead frame, each gas sensor device package of the array of gas sensor device packages including a protuberance.

Embodiment 11: The array of gas sensor device packages of any one of Embodiments 1 through 10, further comprising one or more filters attached to at least one of the protective covering, sidewalls of at least one gas sensor device package of the plurality of gas sensor device packages, or a flame arrestor.

Embodiment 12: The array of gas sensor device packages of Embodiment 11, wherein the one or more filters comprises a unitary material over an upper surface the array of gas sensor device packages.

Embodiment 13: The array of gas sensor device packages of Embodiment 11 or Embodiment 12, wherein the one or more filters comprises at least one dust filter and at least one gas filter.

Embodiment 14: The array of gas sensor device packages of any one of Embodiments 1 through 13, wherein the at least one gas sensor device package comprises a thermoplastic polymer formulated and configured not to outgas volatile organic compounds responsive to exposure to a temperature greater than about 200° C.

Embodiment 15: An array of gas sensor device packages, the array comprising: a plurality of gas sensor device packages within a package material, the package material defining a lead frame for each gas sensor device package of the plurality of gas sensor device packages; each gas sensor device package of the plurality of gas sensor device packages electrically connected to its respective lead frame, each gas sensor device package comprising at least one gas sensor die and a vent through which the gas sensor die is exposed; and a protective material over the vents of the plurality of gas sensor device packages.

Embodiment 16: The array of Embodiment 15, further comprising a flame arrestor covering the vent of each of the plurality of gas sensor device packages.

Embodiment 17: The array of Embodiment 16, wherein the flame arrestor is embedded in a material of sidewalls of the at least one gas sensor device package.

Embodiment 18: The array of Embodiment 16 or Embodiment 17, wherein the flame arrestor is clipped over the at least one gas sensor device package with removable clips.

Embodiment 19: The array of any one of Embodiments 15 through 18, further comprising a metal ring disposed between the at least one gas sensor device package and the flame arrestor.

Embodiment 20: The array of any one of Embodiments 15 through 19, wherein the protective material comprises at least one vent over each gas sensor device package of the array of gas sensor device packages.

Embodiment 21: The array of any one of Embodiments 15 through 20, wherein the cover comprises a lid, wherein the lid comprises at least one protuberance over each gas sensor device package of the array of gas sensor device packages.

Embodiment 22: The array of any one of Embodiments 15 through 21, further comprising one or more filters attached to at least one of the protective material, sidewalls of at least one gas sensor device package of the plurality of gas sensor device packages, or a flame arrestor over the plurality of gas sensor device packages.

Embodiment 23: The array of any one of Embodiments 15 through 22, further comprising saw streets defining and separating each gas sensor device package from other gas sensor device packages of the plurality of gas sensor device packages.

Embodiment 24: A method of fabricating an array of gas sensor device packages, the method comprising: forming an array comprising a package material including a plurality of cavities defined by at least one of saw streets or sidewalls between adjacent cavities; electrically connecting at least one gas sensor die to the package material in at least some of the cavities; and forming at least one of a flame arrestor, at least one filter, or a protective material over the array to form an array of gas sensor device packages.

Embodiment 25: The method of Embodiment 25, wherein forming at least one of a flame arrestor, at least one filter, or a protective material over the array to form an array of gas sensor device packages comprises heating the sidewalls of the package material to a heat deflection temperature thereof and pressing the at least one of the flame arrestor, the at least one filter, or the protective material into the sidewalls.

Embodiment 26: The method of Embodiment 24 or Embodiment 25, further comprising singulating the array of gas sensor device packages to form a plurality of singulated gas sensor device packages.

Embodiment 27: The method of any one of Embodiments 24 through 26, wherein forming at least one of a flame arrestor, at least one filter, or a protective material over the array comprises forming a protective material over the array.

Embodiment 28: The method of Embodiment 27, wherein forming a protective material over the array comprises forming a temporary protective cover over the array, further comprising: attaching the at least one gas sensor die to a printed circuit board; and removing the temporary protective cover from over the at least one gas sensor die after attaching the at least one gas sensor die to the printed circuit board.

Embodiment 29: The method of Embodiment 27, wherein forming a protective material over the array comprises forming a protuberance over at least one of the gas sensor device packages, further comprising: attaching the at least one gas sensor die to a printed circuit board; and cutting the protuberance after attaching the at least one gas sensor die to the printed circuit board.

Embodiment 30: The method of Embodiment 27, wherein forming a protective material over the array comprises forming a thermoplastic material over the array, further comprising: attaching the at least one gas sensor die to a printed circuit board; and puncturing the thermoplastic material after attaching the at least one gas sensor die to the printed circuit board.

Embodiment 31: The method of Embodiment 27, wherein forming a protective material over the array comprises forming a protective material comprising nitrocellulose over the array, further comprising: attaching the at least one gas sensor die to a printed circuit board; and exposing the nitrocellulose to ultraviolet electromagnetic radiation to decompose the protective material after attaching the at least one gas sensor die to the printed circuit board.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following appended claims and their legal equivalents.

What is claimed is:

1. An array of gas sensor device packages, the array comprising:
a plurality of gas sensor device packages, each gas sensor device package comprising a leadframe including bond pads and at least one gas sensor die in electrical communication with the bond pads, the gas sensor device packages each comprising at least one vent;
a protective covering over the plurality of gas sensor device packages; and
a flame arrestor overlying the plurality of gas sensor device packages and bonded to the leadframe at sidewalls of the leadframe, a material of the sidewalls disposed within and surrounding the flame arrestor.

2. The array of gas sensor device packages of claim 1, wherein the flame arrestor comprises a unitary material disposed over the plurality of gas sensor device packages.

3. The array of gas sensor device packages of claim 1, wherein the flame arrestor is coupled to the at least one of the protective covering or sidewalls of at least one gas sensor device package of the plurality of gas sensor device packages with glue, epoxy, or is integral with a thermoplastic material defining the sidewalls.

4. The array of gas sensor device packages of claim 1, wherein the protective covering comprises a temporary protective covering over the vent of at least one gas sensor device package.

5. The array of gas sensor device packages of claim 1, wherein the protective covering comprises a continuous material over the array of gas sensor device packages.

6. The array of gas sensor device packages of claim 1, further comprising saw streets defining individual gas sensor device packages of the array of gas sensor device packages.

7. The array of gas sensor device packages of claim 1, wherein the protective covering covers one or more vents in the plurality of gas sensor device packages.

8. The array of gas sensor device packages of claim 1, wherein the protective covering comprises nitrocellulose.

9. The array of gas sensor device packages of claim 1, wherein the protective covering comprises a protuberance extending in a direction away from the leadframe, each gas sensor device package of the array of gas sensor device packages including a protuberance.

10. The array of gas sensor device packages of claim 1, further comprising one or more filters attached to at least one of the protective covering, sidewalls of at least one gas sensor device package of the plurality of gas sensor device packages, or a flame arrestor.

11. The array of gas sensor device packages of claim 10, wherein the one or more filters comprises a unitary material over an upper surface the array of gas sensor device packages.

12. The array of gas sensor device packages of claim 11, wherein the one or more filters comprises at least one dust filter and at least one gas filter.

13. The array of gas sensor device packages of claim 1, wherein the at least one gas sensor device package comprises a thermoplastic polymer formulated and configured not to outgas volatile organic compounds responsive to exposure to a temperature greater than about 200° C.

14. An array of gas sensor device packages, the array comprising:
a plurality of gas sensor device packages within a package material, the package material defining a leadframe for each gas sensor device package of the plurality of gas sensor device packages;
each gas sensor device package of the plurality of gas sensor device packages electrically connected to its respective leadframe, each gas sensor device package comprising at least one gas sensor die and a vent through which the gas sensor die is exposed;
a protective material over the vents of the plurality of gas sensor device packages; and
a flame arrestor overlying and contacting the leadframe of the respective gas sensor device package.

15. The array of claim 14, wherein the flame arrestor is embedded in a material of sidewalls of the at least one gas sensor device package.

16. The array of claim 14, wherein the flame arrestor is clipped over the at least one gas sensor device package with removable clips.

17. The array of claim 14, further comprising a metal ring disposed between the at least one gas sensor device package and the flame arrestor.

18. The array of claim 14, wherein the protective material comprises at least one vent over each gas sensor device package of the array of gas sensor device packages.

19. The array of claim 14, wherein the protective material comprises a lid, wherein the lid comprises at least one protuberance over each gas sensor device package of the array of gas sensor device packages.

20. The array of claim 14, further comprising one or more filters attached to at least one of the protective material, sidewalls of at least one gas sensor device package of the plurality of gas sensor device packages, or a flame arrestor over the plurality of gas sensor device packages.

21. The array of claim 14, further comprising saw streets defining and separating each gas sensor device package from other gas sensor device packages of the plurality of gas sensor device packages.

22. A method of fabricating an array of gas sensor device packages, the method comprising:

forming an array comprising a package material comprising a leadframe including a plurality of cavities defined by at least one of saw streets or sidewalls between adjacent cavities;

electrically connecting at least one gas sensor die to the leadframe in at least some of the cavities to form an array of gas sensor device packages; and forming a flame arrestor over the array of gas sensor device packages, the flame arrestor bonded to sidewalls of the leadframe, a material of the sidewalls disposed within and surrounding the flame arrestor.

23. The method of claim 22, wherein forming at least one of a flame arrestor, at least one filter, or a protective material over the array to form an array of gas sensor device packages comprises heating the sidewalls of the package material to a heat deflection temperature thereof and pressing the at least one of the flame arrestor, the at least one filter, or the protective material into the sidewalls.

24. The method of claim 22, further comprising singulating the array of gas sensor device packages to form a plurality of singulated gas sensor device packages.

25. The method of claim 22, wherein forming at least one of a flame arrestor, at least one filter, or a protective material over the array comprises forming a protective material over the array.

26. The method of claim 25, wherein forming a protective material over the array comprises forming a temporary protective cover over the array, further comprising:

attaching the at least one gas sensor die to a printed circuit board; and removing the temporary protective cover from over the at least one gas sensor die after attaching the at least one gas sensor die to the printed circuit board.

27. The method of claim 25, wherein forming a protective material over the array comprises forming a protuberance over at least one of the gas sensor device packages, further comprising:

attaching the at least one gas sensor die to a printed circuit board; and cutting the protuberance after attaching the at least one gas sensor die to the printed circuit board.

28. The method of claim 25, wherein forming a protective material over the array comprises forming a thermoplastic material over the array, further comprising:

attaching the at least one gas sensor die to a printed circuit board; and puncturing the thermoplastic material after attaching the at least one gas sensor die to the printed circuit board.

29. The method of claim 25, wherein forming a protective material over the array comprises forming a protective material comprising nitrocellulose over the array, further comprising:

attaching the at least one gas sensor die to a printed circuit board; and exposing the nitrocellulose to ultraviolet electromagnetic radiation to decompose the protective material after attaching the at least one gas sensor die to the printed circuit board.

\* \* \* \* \*